US006979568B1

(12) United States Patent
Nakajima et al.

(10) Patent No.: US 6,979,568 B1
(45) Date of Patent: Dec. 27, 2005

(54) VECTOR FOR THE EXPRESSION OF TWO FOREIGN GENES

(75) Inventors: Toshihiro Nakajima, Hyogo (JP); Kenji Nakamaru, Tokyo (JP); Mamoru Hasegawa, Ibaraki (JP); Masanori Hayami, Kyoto (JP); Eiji Ido, Kyoto (JP)

(73) Assignee: DNAVEC Research, Inc., Ibaraki (JP)

( * ) Notice: Subject to any disclaimer, the term of this patent is extended or adjusted under 35 U.S.C. 154(b) by 381 days.

(21) Appl. No.: 09/980,420

(22) PCT Filed: Jun. 16, 2000

(86) PCT No.: PCT/JP00/03955

§ 371 (c)(1),
(2), (4) Date: Jun. 5, 2002

(87) PCT Pub. No.: WO00/78987

PCT Pub. Date: Dec. 28, 2000

(30) Foreign Application Priority Data

Jun. 22, 1999 (JP) .................................. 11/175646

(51) Int. Cl.$^7$ .......................... C12N 15/11; C12N 15/64; C12N 15/86; C12N 7/01; C12P 19/34; C07H 21/04; A01N 48/00
(52) U.S. Cl. ................. 435/320.1; 435/91.1; 435/91.4; 435/91.41; 435/91.42; 435/455; 435/456; 435/457; 435/235.1; 536/23.1; 536/23.72; 536/24.1; 424/93.2
(58) Field of Search ............................... 435/456, 91.1, 435/91.4, 91.41, 91.42, 235.1, 320.1, 455, 435/457; 536/23.1, 23.72, 24.1; 424/93.2

(56) References Cited

U.S. PATENT DOCUMENTS 5,994,136 A * 11/1999 Naldini et al. ............... 435/455

FOREIGN PATENT DOCUMENTS

| WO | WO 97/12622 | 4/1997 |
| WO | WO 99/15683 A1 | 4/1999 |
| WO | WO 99/31251 | 6/1999 |
| WO | WO 00/29421 | 5/2000 |
| WO | WO 00/29557 | 5/2000 |

OTHER PUBLICATIONS

Dull et al., "A Third-Generation Lentivirus Vector with a Conditional Packaging System," *J. Virol.*, 72:8463-8471 (1998)

Zufferey et al., "Self-Inactivating Lentivirus Vector for Safe and Efficient in vivo Gene Delivery," *J. Virol.*, 72:9873-9880 (1998).
Farson et al., "A New-Generation Stable Inducible Packaging Cell Line for Lentiviral Vectors," *Human Gene Therapy* 12:981-997 (2001).
Nakajima et al., "Development of Novel Simian Immunodeficiency Virus Vectors Carrying a Dual Gene Expression System," *Human Gene Therapy*, 11:1863-1874 (2000).
Rappa et al., "Novel Bicistronic Retroviral Vector Expressing γ-Glutamylcysteine Synthetase and the Multidrug Resistance Protein 1 (MRP1) Protects Cells from MRP1-Effluxed Drugs and Alkylating Agents," *Human Gene Therapy* 12:1785-1796 (2001).
Barksdale and Baker, "The Human Immunodeficiency Virus Type 1 Rev Protein and the Rev-Responsive Element Counteract the Effect of an Inhibitory 5' Splice Site in a 3' Untranslated Region," *Mol. Cell. Biol.*, 15(6):2962-2971, 1995.
Brighty and Rosenberg, "A Cis-Acting Repressive Sequence that Overlaps the Rev-Responsive Element of Human Immunodeficiency Virus Type 1 Regulates Nuclear Retention of *env* mRNAs Independently of Known Splice Signals," *Proc. Natl. Acad. Sci. USA*, 91(18):8314-8318, 1994.
Dougherty and Temin, "High Mutation Rate of a Spleen Necrosis Virus-Based Retrovirus Vector," *Mol. Cell. Biol.*, 168(3):4387-4395, 1986.
Korman et al., "Expression of Human Class II Major Histocompatibility Complex Antigens Using Retrovirus Vectors," *Proc. Natl. Acad. Sci. USA*, 84(8):2150-2154, 1987.
Naldini et al., "In Vivo Gene Delivery and Stable Transduction of Nondividing Cells by a Lentiviral Vector," *Science*, 272(5259):263-267, 1996.

* cited by examiner

*Primary Examiner*—David Guzo
*Assistant Examiner*—Michael D. Burkhart
(74) *Attorney, Agent, or Firm*—Clark & Elbing LLP

(57) ABSTRACT

A vector expressing two foreign genes by using RRE sequence and controlling the ratio of the expression doses of these genes owing to the modification is provided. This vector, which can be provided as a lentivirus vector based on SIVagm, is constructed by modifying a virus-origin expression regulatory sequence into another expression regulatory sequence so as to eliminate the dependency on the virus-origin protein. Although this vector has a packaging signal, it has been modified so that the risk of the occurrence of wild strains due to gene recombination is lowered and no virus structural protein is expressed. This vector is highly useful as a gene therapeutic vector with a need for transferring two genes while controlling the expression doses or expression dose ration thereof.

Figure 1:
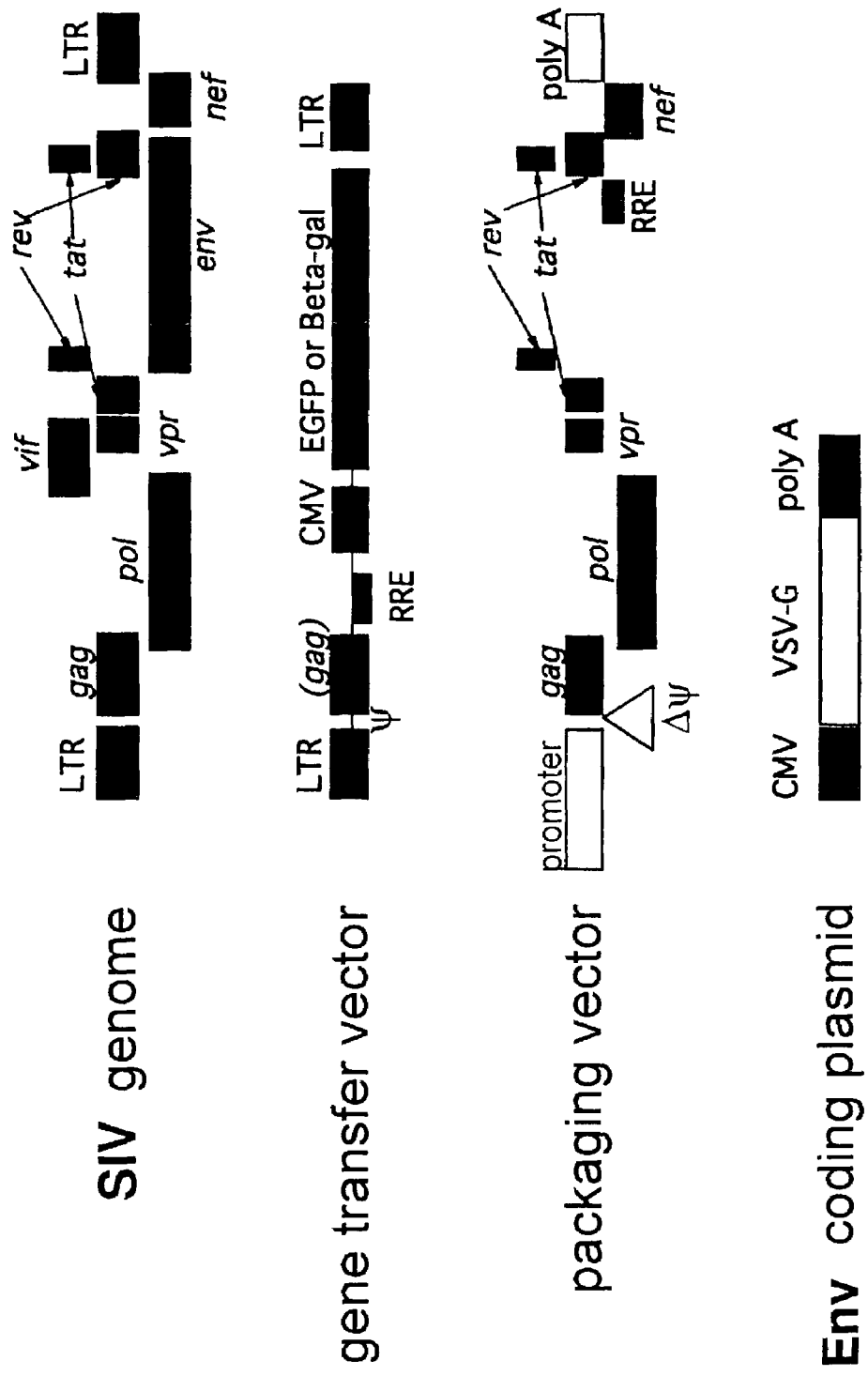

28 Claims, 17 Drawing Sheets vector containing DNA fragments
of LTR-gag region in various length

↓ testing their packaging by $\beta$-galactosidase assay

VECTOR FOR THE EXPRESSION OF TWO FOREIGN GENES

The application claims priority from international patent application serial number PCT/JP00/03955, filed on Jun. 16, 2000, which, in turn, claims priority from Japanese patent application No. 11/175,646, filed on Jun. 22, 1999, the disclosures of which are hereby incorporated by reference.

TECHNICAL FIELD

This invention relates to a vector for expressing foreign genes.

BACKGROUND ART

Gene transferring vectors are used in research and gene therapy to express foreign genes in target cells. In such situations, it is sometimes desirable that two genes be expressed in the same target cell. This will allow, for example the selective proliferation or death of target cells to which therapeutic genes have been inserted by expressing therapeutic genes in combination with selective genes. Alternatively, this will allow the monitoring of the dynamics of a therapeutic transgenic cell in vivo by expressing marker genes (e.g., GFP etc.) in combination with therapeutic genes. Furthermore, this will allow the expression of proteins that function by forming a complex between two types of subunits, such as receptors and transcription factors.

Previously, as vector systems for coexpression of two genes, a form in which multiple promoters are inserted, and another form in which one promoter is combined with an IRES (Internal Ribosomal Entry Site) sequence have been reported. However, the expression properties of these vectors are by no means satisfactory.

For example, vectors having multiple promoters suffer from the problem of efficient expression from only one of the promoters due to interference among the promoters. Alternatively, vectors with a combination of one promoter and an IRES sequence contain the problem that the expression level of genes on the 3' side from IRES is only ⅕ to 1/10 of that on the 5' side from IRES.

DISCLOSURE OF THE INVENTION

The object of this invention is to provide a vector that allows the coexpression of two foreign genes. More specifically, the object of present invention is to provide a vector that allows the coexpression of two foreign genes using an RRE sequence and that allows the regulation of the ratio of expression level of the two foreign genes by alteration of the RRE sequence.

In a preferred embodiment, a virus vector is provided in which a virus-derived expression regulatory sequence is altered to another expression regulatory sequence, such that the dependence on virus-derived proteins is eliminated. In another preferred embodiment, a virus vector with a packaging signal is provided, wherein the vector is altered so that the risk of generation of a wild-type strain due to gene recombination is decreased, and further wherein a virus structural protein is not expressed.

The present inventors generated a novel virus vector using RRE and a simian immunodeficiency virus (SIV) having various advantages, such as better safety as compared to the human immunodeficiency virus (HIV) conventionally used in the field of gene therapy.

Specifically, a vector containing a 5'LTR region, RRE, CMV promoter, EGFP gene (or β-galactosidase gene), and 3'LTR in order was first constructed as a gene transfer vector based on SIVagmTY01, which is a clone of a non-pathogenic African Green Monkey immunodeficiency virus.

Since a trans-acting virus structural protein towards a gene transfer vector in a packaging cell is required for packaging of a gene transfer vector into a vector particle, the present inventors also constructed a packaging vector for providing a virus structural protein within the packaging cell. That is, a vector expressing a virus exodermal protein (VSV-G) within the packaging cell, and a vector expressing a virus core protein (gag) and a reverse transcriptase (pol) therein were constructed.

The transcription activity of a lentiviral 5'LTR is generally dependent on a Tat protein, which is a virus-derived factor. Therefore, the present inventors subsequently produced a gene transfer vector in which the U3 region, the promoter sequence of 5'LTR, is replaced with another promoter sequence in order to eliminate the dependence of the generated gene transfer vector on the Tat protein and to increase the vector titer by replacement with a promoter sequence having stronger transcription activity, thereby providing a Tat-independent vector.

In the lentivirus vector, it is found that, since the U3 region, a promoter sequence contained in the 3'LTR region, is inserted into the U3 promoter region of 5'LTR upon reverse transcription in the target cell, the U3 region contained in the 3'LTR region of the gene transfer vector plasmid functions as the U3 promoter of 5'LTR, relating to gene expression in the target cell genome. Therefore, a vector in which the U3 region of 3'LTR in the gene transfer vector is replaced with another promoter sequence was produced to determine whether the promoter relating to gene expression within the target cell can be replaced with promoters other than those having a U3 sequence. In addition, to determine whether the promoter sequence in the 5'LTR within the target cell can be simultaneously deleted, a vector, in which the U3 region of 3'LTR in the gene transfer vector is deleted, was produced.

A packaging signal, which is a cis-acting factor on a gene transfer vector, is required for packaging into a vector particle of a gene transfer vector, and moreover, by enhancing the packaging efficiency of the vector, vector titer will be elevated. Therefore, as long the region containing the packaging signal as possible should be inserted so that the structure formed by the packaging signal sequence can be maintained. However, on the other hand, the generation frequency of a wild-type virus due to recombination, which may occur between the two sequences, should be suppressed to a minimum by minimizing sequence overlap between the packaging signal of the gene transfer vector and the packaging vector. Therefore, in order to construct a vector system, it is necessary to identify correctly the minimal packaging signal sequence required for efficient packaging of a gene transfer vector. Thus, the present inventors inserted DNA fragments containing different lengths of the region downstream of 5'LTR into a gene transfer vector to provide a vector that was both safety and packaging ability.

Next, the present inventors generated a virus vector that allows the coexpression of two foreign genes simultaneously. The Rev responsive element (RRE) is a virus-derived Rev protein binding site which is involved in transport of RNA from the nucleus to the cytoplasm. Using this RRE/Rev system, it was examined whether a system that coexpresses two different types of proteins from a single promoter may be generated through the regulation of splicing efficiency.

First, to examine whether expression of two different types of proteins can be regulated by RRE, a vector was generated, wherein the luciferase gene and the β-galactosidase gene were inserted upstream and downstream of RRE, respectively, as reporter genes, a splicing donor sequence was inserted upstream of the luciferase gene, and a splicing acceptor sequence was inserted downstream of the RRE sequence. It was expected that the spliced mRNA would express the β-galactosidase protein and that the unspliced mRNA would express the luciferase protein, from this vector.

Further, in order to examine not only the expression of two different genes, but also the regulation of the ratio of their expression level by changing the sequence of RRE, 6 types of RRE sequence-inserted vectors were generated to determine the expression levels of the reporter genes in each of these vectors.

As a result, it was found that two different types of genes can be expressed from a vector containing an RRE sequence, and that expression efficiency of two types of genes can be regulated by replacement of the RRE sequence. In addition, since two different types of genes are expressed in the absence of a packaging vector, it was found that present gene expression system may express two types of genes independently of the presence of a Rev protein.

Previously, it was thought that RRE effects depend on Rev protein, and that the regulation by Rev/RRE is an "all or nothing" situation. Thus, all would be in the spliced form under Rev-, and in the non-spliced form under Rev+. That is, there had been no examples in which changing of the RRE sequence results in changes in the ratio of splicing. Therefore, the above-mentioned results demonstrate for the first time that the ratio of splicing can be changed by altering the RRE sequence.

Furthermore, the present inventors examined whether the coexpression system for two types of genes using RRE can be applied to an expression system using various promoters other than 5'LTR. Other promoters derived from human cytomegalovirus (CMV) and promoters derived from mammal cells (EF1α promoter) were used. As a result, it was found that even when promoters other than 5'LTR are used, two types of genes can be expressed simultaneously. In addition, it was found that regulation of the expression level of two types of genes was dependent on an RRE sequence. Therefore, the coexpression system for two types of genes using RRE was found to be widely useful, in expression systems using various promoters.

In addition, the different expression level of each gene, depending on whether the reporter gene is inserted upstream or downstream of RRE, was examined. Vectors, in which luciferase and β-galactosidase were instituted with each other in a gene transfer vector, were produced to compare the expression levels of two types of reporter genes in both vectors. As a result, no differences were observed in the expression levels of the reporter genes, whether they were inserted upstream or downstream of RRE.

As mentioned above, the present inventors succeeded in generating a novel virus vector that enabled two genes to be coexpressed using the RRE sequence and that enabled the regulation of the expression ratio of the two genes, owing to the difference in the RRE sequence used, thereby completing this invention.

More specifically, this invention relates to,
(1) a vector DNA for expressing two foreign genes, said vector DNA comprising the following components in order from the 5' side to the 3' side:
   (a) an expression regulatory sequence;
   (b) a splicing donor sequence;
   (c) a first foreign gene insertion site;
   (d) an RRE core sequence;
   (e) a splicing acceptor sequence; and
   (f) a second foreign gene insertion site;
(2) a vector DNA for expressing two foreign genes, said vector DNA comprising the following components in order from the 5' side to the 3' side:
   (a) an expression regulatory sequence;
   (b) a splicing donor sequence;
   (c) an RRE core sequence;
   (d) a first foreign gene insertion site;
   (e) a splicing acceptor sequence; and
   (f) a second foreign gene insertion site;
(3) the vector DNA according to (1) or (2), wherein the RRE core sequence is derived from a retrovirus;
(4) the vector DNA according to (1) or (2), wherein the RRE core sequence is derived from a lentivirus;
(5) the vector DNA according to (1) or (2), wherein the RRE core sequence is derived from an immunodeficiency virus;
(6) the vector DNA according to any one of (1) to (5), wherein the expression regulatory sequence comprises an LTR;
(7) the vector DNA according to any one of (1) to (6), wherein the expression regulatory sequence is a sequence comprising an expression regulatory sequence other than LTR;
(8) the vector DNA according to (7), wherein the expression regulatory sequence other than LTR is selected from the group consisting of the CMVL promoter, the CMV promoter, and the EF1α promoter;
(9) the vector DNA according to any one of (1) to (8), wherein the splicing donor sequence and the splicing acceptor sequence are derived from a retrovirus;
(10) the vector DNA according to any one of (1) to (8), wherein the splicing donor sequence and the splicing acceptor sequence are derived from a lentivirus;
(11) the vector DNA according to any one of (1) to (8), wherein the splicing donor sequence and the splicing acceptor sequence are derived from an immunodeficiency virus;
(12) the vector DNA according to any one of (1) to (11), wherein said vector DNA further comprises a packaging signal in a region thereon that can be transcribed;
(13) the vector DNA according to (12), wherein the packaging signal is derived from a retrovirus;
(14) the vector DNA according to (12), wherein the packaging signal is derived from a lentivirus;
(15) the vector DNA according to (12), wherein the packaging signal is derived from an immunodeficiency virus;
(16) the vector DNA according to any one of (13) to (15), wherein said vector DNA is constructed so as not to express a complete gag protein;
(17) the vector DNA according to any one of (13) to (16), wherein the translation initiation codon of the gag protein is mutated;
(18) the vector DNA according to any one of (1) to (17), wherein a first foreign gene and a second foreign gene are inserted into said vector DNA;
(19) a retrovirus vector comprising, within a virus particle thereof, a transcription product from the vector DNA according to any one of (12) to (17), wherein a first foreign gene and a second foreign gene have been inserted into said vector DNA;

(20) a lentivirus vector comprising, within a virus particle thereof, a transcription product from the vector DNA according to any one of (12) to (17), wherein a first foreign gene and a second foreign gene have been inserted into said vector DNA;

(21) an immunodeficiency virus vector comprising, within a virus particle thereof, a transcription product from the vector DNA according to any one of (12) to (17), wherein a first foreign gene and a second foreign gene have been inserted into said vector DNA; and

(22) a method for preparing a virus vector, said method comprising the steps of introducing into a packaging cell the vector DNA according to any one of (12) to (17), wherein a first foreign gene and a second foreign gene are inserted into said vector DNA, and collecting produced virus particles from a culture supernatant of said cell.

Herein, "virus vector" refers to a virus particle containing packaged nucleic acid molecules for expression of foreign genes in a host.

According to this invention, the vector DNA, comprising (a) an expression regulatory sequence, (b) a splicing donor sequence, (c) a first foreign gene insertion site, (d) an RRE core sequence, (e) a splicing acceptor sequence, and (f) a second foreign gene insertion site in this order, is used for expressing two foreign genes (note: elements (c) and (d) may be interchanged).

Once inserted into this vector DNA, two foreign genes can be coexpressed, depending on whether spliced or not. The theory underlying the invention is described as follows.

Once the vector DNA to which two foreign genes have been inserted is introduced into an appropriate host cell, a transcription product, comprising in order: a splicing donor sequence, a first foreign gene, an RRE core sequence, a splicing acceptor sequence, and a second foreign gene, is produced due to the activation of an expression regulatory region. From this transcription product, if splicing does not occur between the splicing donor sequence and the splicing acceptor sequence, mRNA encoding only the first foreign gene is produced. Because the ribosome that translated the first foreign gene encoded in the mRNA leaves the RNA due to the stop codon of the first foreign gene, translation of the second gene will not occur. On the other hand, when splicing occurs between the splicing donor sequence and the splicing acceptor sequence, mRNA from which only the second foreign gene can be translated is produced by deletion of a region containing the first foreign gene. Therefore, two gene products can be expressed in the host cell to which the vector DNA was inserted due to the presence or absence of this splicing.

The type of expression regulatory sequence used on the vector DNA of this invention is not limited to LTR. However, for use of a virus vector as follows, a reverse transcribed virus genome must function to be incorporated itself into a chromosome of a host upon infection of a virus to a target cell. As examples of expression regulatory sequence carrying such a function other than LTR, chimeric promoters composed with LTR and other promoters, described in the examples, can be given.

The use of a normal combination of splicing donor sequence and acceptor sequence as those to be applied to the vector DNA of this invention is not preferred since splicing will occur with a nearly 100% efficiency. In the present invention, the sequence is suitable wherein two or more types of proteins express from one type of RNA by the difference in splicing. Generally, it is known that there are many such sequences in retroviruses (A. B. Rabson and B. J. Graves, "Synthesis and Processing of Viral RNA", in "Retroviruses", pp. 205–262 (1997) eds. J. M. Coffin, S. H. Hughes, and H. E. Varmus, Cold Spring Harbor Laboratory Press). Examples include the region from base 6964 to base 8177 in the genomic sequence of SIVagm TYO1, shown in SEQ ID NO: 76.

The first foreign gene insertion site in the vector DNA of the present invention should be positioned between the splicing donor sequence and the splicing acceptor sequence. The first foreign gene insertion site can be produced by inserting an appropriate restriction enzyme site that does not inhibit the translation of a target gene. The second foreign gene insertion site can be produced by inserting an appropriate restriction enzyme site so that it is positioned between the splicing acceptor sequence and poly-A addition signal. As long as the expression of the first foreign gene is not inhibited, an RRE sequence may be positioned at the 5'side or the 3'side of the insertion site of the first foreign gene.

There are no particular restrictions on the combination of first and second foreign genes. Examples of combinations of two types of genes that are considered useful are shown below.

a) A Therapeutic Gene and a Drug Resistant Marker

By selecting only the therapeutic transgenic cells using the appropriate agent in vivo, nontransgenic cells are decreased while transgenic cells are increased.

b) A Therapeutic Gene and a Growth Factor or its Receptor

By stimulating the growth of therapeutic transgenic cells, only the transgenic cells can be selectively proliferated to enhance the therapeutic effect.

c) A Therapeutic Gene and a Homing Receptor

For the specific delivery of therapeutic transgenic cells to the desired site, a homing receptor is coexpressed, such as an AIDS therapeutic gene and a homing receptor for lymph nodes.

d) A Therapeutic Gene and a Marker Gene

The dynamics and half-life of a therapeutic transgenic cell with a marker may be constantly monitored. If a protein can be detected extracorporeally, constant extracorporeal monitoring of transgenic cells may be performed.

e) Expression of a Protein Consisting of Two Types of Subunits

It has been elucidated that various proteins form heterodimers. Since the vector DNA of the present invention enables such proteins to be expressed, the choice of therapeutic genes will expand beyond those available in the past.

f) Expression of Two Types of Interacting Genes

A pair of a ligand and a receptor, a pair of an enzyme and its substrate, a pair of a signal transduction molecule and its receptor, and such can be expressed. For example, coexpression of a growth factor and its receptor can increase the number of transgenic cells remarkably.

g) Expression of Two Types of Genes Having Synergistic Effect

In various signal transduction systems, synergistic effects, for example, synergistic effects occurred by stimuli from two types of ligands, are often observed due to activation of multiple signal transduction systems. By expression of two types of genes having such effect, therapeutic effect may be elevated.

In addition, splicing efficiency of the transcription product can be regulated by modifying the RRE sequence on the vector DNA of present invention, and thus, the quantitative ratio of two gene products expressed in the host cells can be regulated. Furthermore, the amount of the gene product itself can be regulated.

Figure 8:
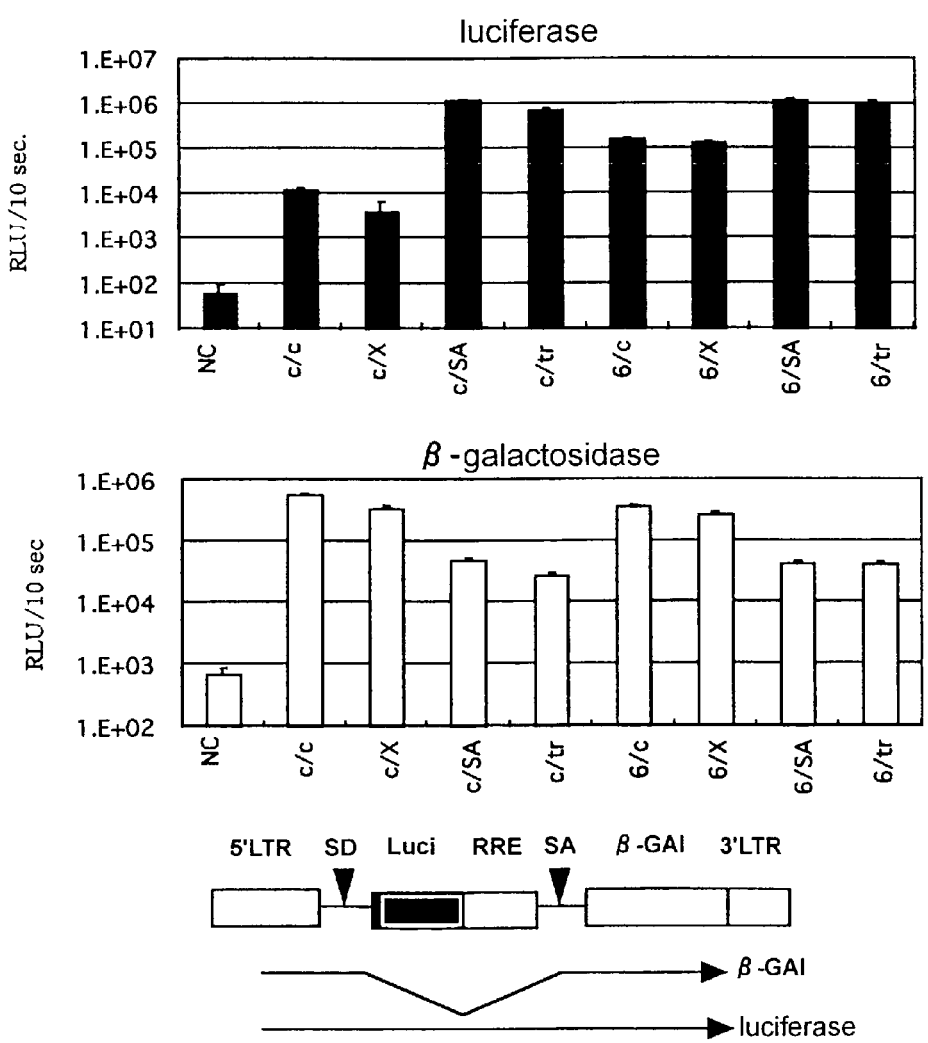

For example, as indicated in FIG. 8, the expression ratio of the first foreign gene can be elevated by using c/SA or c/tr sequence as a RRE sequence; conversely, expression ratio of the second foreign gene can be elevated by using c/c or c/x sequence as a RRE sequence. In addition, as shown in FIG. 8, the expression level itself of the foreign gene can be altered by using different RRE sequences. Various advantages exist in the regulation of expression level of foreign genes. For example, as optimal expression levels exist for expression levels of two types of gene products when expressing them in gene therapy, therapeutic effect may be elevated by regulation to the optimal expression levels via control of the quantitative ratio. For example, for a heterodimer, the expression of each polypeptide, subunits of a heterodimer, in a quantitative ratio of 1:1 is thought to be most efficient, while for an enzyme and a substrate, it is thought that efficiency will rise if the amount of enzyme is reduced and that of substrate is increased.

The method for introducing the vector in vivo of present invention can be performed as described below, for example.

a) Administering a DNA Itself

Since administration to muscle cells can be performed with DNA alone, DNA itself may be administered as a vector.

b) Administering a Nonviral Vector

DNA may be administered in the form of a complex with a synthesized compound for transfection, such as lipofectamine or polycationic liposome.

c) Administering a Viral Vector

DNA may be administered via insertion into a DNA-type viral vector, such as an adenovirus.

For producing a virus particle packaged with the vector DNA of the present invention, a packaging signal is required in a region on the vector DNA that can be transcribed. As long the region containing the packaging signal as possible should be inserted into the vector so as to maintain the structure formed by the packaging signal sequence. On the other hand, to suppress the generating frequency of a wild-type virus due to recombination between the packaging signal and the packaging vector on the vector DNA, overlap of sequences between these vectors should be kept to a minimum. Therefore, in generating the vector DNA of this invention, it is preferable to use a sequence that contains the necessary sequence for packaging but, at the same time, is as short a sequence as possible, so that both packaging efficiency and safety are maximized.

As a packaging signal, there is no limitation, so long as the packaging vector is packaged by the transfected cell. Thus, retrovirus-derived, lentivirus-derived, immunodeficiency virus-derived signals, and such can be used, depending on the type of packaging vector.

For example, when using a packaging vector derived from SIVagm as described in the examples, signals that can be used will be derived from only SIV, since HIV vector is not packaged. However, when an HIV-derived packaging vector is used, because SIV-derived gene transfer vector is also packaged, a different lentivirus-derived gene transfer vector and packaging vector may be combined to produce a vector particle in order to reduce the generation frequency of recombined viruses. In this case, a combination between lentiviruses of primates (e.g., HIV and SIV) is preferred.

In the vector DNA of this invention, alteration for preventing the expression of a gag protein is preferred. Viral gag protein can be recognized as a foreign substance in vivo, thereby resulting in antigenicity. It may also affect cell function. Therefore, in the gene transfer vector of this invention, it is preferred that gag protein is altered to prevent the expression.

To prevent the expression of the gag protein, a modification can be carried out to cause a frame shift by deletion, addition, and such of bases downstream of the initiation codon of gag. In addition, partial deletion of a gag protein-coding region is preferred. For packaging of viruses, the 5' side of the gag protein-coding region is considered to be necessary. Therefore, the gene transfer vector of this invention is preferred have the C-terminal region of the gag protein-coding region deleted therefrom. Preferably, the gag-coding region that is deleted is as wide as possible, without having a large effect on packaging efficiency. Specifically, the region 3' side downstream of 150 bp of the gag-coding region can be deleted. In addition, replacement of the gag protein initiation codon (ATG) to a codon other than ATG is also preferred. A codon to be replaced is preferably one that has little effect on packaging efficiency. By introducing the vector DNA of this invention, having a packaging signal constructed as above, into an appropriate packaging cell, virus vectors can be produced. The produced virus vectors can be collected from the culture supernatant of the packaging cells.

There are no limitations on cells to be used as packaging cells, as long as they are cell lines generally used to produce viruses. For applications in gene therapy for human, the appropriate origin of the cell may be human or monkey. Human cell lines that may be used as packaging cells are, for example, 293 cells, 293T cells, 293EBNA cells, SW480 cells, u87MG cells, HOS cells, C8166 cells, MT-4 cells, Molt-4 cells, and such. Examples of monkey-derived cell lines are COS1 cells, COS7 cells, CV-1 cells, BMT10 cells, and such.

Because they enable integration of genes into non-dividing cells, the vectors of this invention, produced based on lentiviruses such as HIV, SIV, and FIV, contribute to elevation of effectiveness of gene therapy beyond the limitations of the conventional gene therapy by retroviral vectors. That is, integration of various therapeutic genes to chromosomes of non-dividing cells becomes possible by the vectors of this invention.

This invention may also be applied to gene therapy of various genetic diseases. Examples of targeted diseases and their causative gene for gene insertion into a chromosome are as follows: β-cerebrosidase gene (chromosome 20) for Gaucher's disease, blood coagulation factor 8 (X chromosome) and blood coagulation factor 9 (chromosome X) for hemophilia, adenosine deaminase gene for adenosine deaminase deficiency, phenylalanine hydroxylase gene (chromosome 12) for phenylketonuria, dystrophin gene (chromosome X) for Duchenne dystrophy, LDL receptor gene (chromosome 19) for familial hypercholesterolemia, CFTR gene for cystic fibrosis, and such. The targeted disease in which other multiple genes are thought to be involved include neurodegenerative diseases such as Alzheimer's disease and Parkinson's disease, ischemic encephalopathy, dementia, and intractable infection such as AIDS. A treatment to inactivate the HIV transcription factor may be considered, wherein an SIV based vector of this invention is worked in vitro into a hematopoietic stem cell removed from an AIDS patient extracellularly, for increasing the transcription of SIV-derived genome prior to HIV infection, and the transfected cell is returned to the patient's body. Furthermore, examples of applications possible for chronic diseases include: suppression of the expression of VEGF and FGF2 genes for ischemic heart disease, and suppression of the expression of cell proliferation related genes, such as cell proliferation factors (PDGF, TGF-β, etc.) and cyclin-dependent kinase, for gene therapy of arteriosclerosis. In addition, for diabetes, the BDNF gene may be a candidate. Furthermore, this method can be applied to substitution therapy, in which a gene such as a cancer suppressor gene, p53, whose genetic mutation causes canceration, is integrated into the chromosome, and this method enables treatment beyond the limitation of cancer pharmacotherapy by introducing a multiple-drug-resistant gene into bone marrow-derived hematopoietic stem cells in vitro and, then, by returning these cells into patient's blood. Regarding gene therapy of autoimmune diseases such as multiple sclerosis, chronic rheumatoid arthritis, SLE, and glomerulonephritis, expression suppression by antisense expression of T-cell receptors, various adhesion factors (for example, ICAM-1, LFA-1, VCAM-1, and LFA-4 etc.), cytokines and cytokine receptor (for example, TNF, IL-8, IL-6, and IL-1 etc.) cell proliferation factors (for example, PDGF, and TGF-β etc.), and activation factors (for example, MMP etc.) become possible. Regarding gene therapy of allergic diseases, expression suppression by antisense expression of IL-4, FcεR-I, and such becomes possible. Regarding gene therapy relating to organ transplantation, the elevation of success percentage of a xenotransplant becomes possible by changing the histocompatibility antigen of a non-human animal donor to a human-type. Furthermore, treatment by introducing foreign genes into the chromosome of human ES cells, thus making up the deficient genes at the embryonic stage to supplement deficiencies of systemically circulating enzymes, growth factors, and such may be considered.

BRIEF DESCRIPTION OF THE DRAWINGS

FIG. 1 is a diagram showing an outline of a lentivirus vector system using the monkey immunodeficiency virus clone SIVagmTYo1.

FIG. 2 is a structural diagram of the SIVagm gene transfer vector in which the U3 region, 5' LTR promoter sequence, was substituted with other promoter sequence.

FIG. 3 is a diagram showing the structure of the SIVagm gene transfer vector, in which the U3 region of 3' LTR has been substituted with other promoter sequences, and the structure of U3 promoter region of 5' LTR that is expected to be produced as a result of reverse transcription of the vector in target cells.

FIG. 4 is a conceptual diagram of a method for identifying a packaging signal for the gene transfer vector.

FIG. 5 is a conceptual diagram of a method for identifying a packaging signal, using a mutant produced by point mutation at the position of translation initiation codon for gag protein in the gene transfer vector.

FIG. 6 is a structural diagram of vector for the coexpression of two genes using RRE. Upstream and downstream of RRE, the luciferase gene and β-galactosidase gene are inserted as reporter genes, respectively. Further a splicing donor sequence is inserted upstream of the luciferase gene and a splicing acceptor sequence is inserted downstream of the RRE. Two types of mRNA are produced from the vector depending on the presence or absence of the splicing event.

FIG. 7 is a structural diagram of vectors having various RRE sequences.

FIG. 8 shows a result obtained by the measurement of expression levels of the two genes on the vectors having the 5'LTR as a promoter and various RRE sequences.

FIG. 9 shows gene expression in the two-gene coexpression system constructed with various types of promoters except the 5' LTR in the panel. Human cytomegalovirus (CMV)-derived promoter and mammalian cell-derived promoter (EF1α promoter) were used as the promoters. A structural diagram for the vector is shown in the lower panel.

FIG. 10 shows two gene coexpression vectors, wherein its reporter genes β-galactosidase and luciferase are substituted with each other or not (lower panel). Both are SIVagm gene transfer vectors and containing RRE6/s (6964–7993) sequence. The graph shows a result of comparison of expression levels between two reporter genes on each vector.

FIG. 11 shows photographs obtained with a fluorescence microscope for the expression of the EGFP gene introduced using the SIVagm SIN vector, into 293T cells in arrested state at G2-M phase (A) and into SH-SY5Y cells in which differentiation had been induced by retinoic acid (B).

FIG. 12 shows diagrams analyzing by flow cytometry the expression of the EGFP gene introduced into human PBMC using the SIVagm vector. The longitudinal axis indicates the cell count and the horizontal axis indicates fluorescence intensity corresponding the expression level of EGFP. The cells in the area of M1 are EGFP positive, and the numerical value in the diagram represents the EGFP-positive percentage (%).

FIG. 13 shows diagrams analyzing by flow cytometry the expression of EGFP gene introduced into T cells derived from human PBMC using the SIVagm vector FIG. 14 shows diagrams analyzing by flow cytometry the expression of EGFP gene introduced into CD34 positive cells derived from human bone marrow using the SIVagm vector. The analysis was performed with a series of two colors corresponding to EGFP and PE to determine the EGFP-positive ratio. The cells in the R2 area are GFP positive, and the numerical value in the diagram represents the EGFP-positive percentage (%).

FIG. 15 is a diagram analyzing by flow cytometry the expression of the EGFP gene introduced into CD34 positive cells derived from human umbilical blood using the SIVagm vector.

FIG. 16 shows diagrams analyzing by flow cytometry the expression of the EGFP gene introduced into CD34 positive cells derived from cynomolgus monkey bone marrow using the SIVagm vector.

FIG. 17 shows diagrams analyzing by flow cytometry the percentage of the human cells in the peripheral blood five and six weeks after human umbilical blood-derived CD34 positive cells into which the EGFP gene had been introduced using the SIVagm vector were transplanted in NOD/SCID mice. The human lymphocytes were stained with a PE-labeled anti-human CD45 antibody in mouse peripheral blood leukocytes, followed by the two-color analysis with EGFP. UL, UR, LL and LR represent upper left, upper right, bottom left and bottom right areas in each diagram, respectively. Cells in UL and UR areas are CD45 positive, and those in UR area are both of CD45 and EGFP positive. The numerical value in the diagram represents percentage (%) of the number of cells contained in each area relative to the total cell count.

BEST MODE FOR CARRYING OUT THE INVENTION

The present invention is illustrated in detail below with reference to Examples, but should not be limited thereto.

EXAMPLE 1

Generation of SIVagm Vector and the Verification of its Performance

Generation of novel lentivirus vector was carried out as follows, using SIVagmTYO1, which is a nonpathogenic immunodeficiency virus clone derived from monkey. The outline of vector system is shown in FIG. 1.

SIVagmTYO1 comprising a clone of nonpathogenic immunodeficiency virus derived from African green monkey was used in the generation of vector system. Hereinafter, all nucleotide numbers are indicated with the transcription initiation site of the virus RNA as +1. pSA212 (J. Viol., vol. 64, pp 307–312, 1990) was used as a plasmid, in which SIVagmTYO1 had been inserted. Further, all ligation reactions were carried out using a Ligation High (Toyobo) according to the attached instruction.

a. Generation of a Packaging Vector

First, a DNA fragment corresponding to a region (5337–5770) containing vif and the first exon of tat/rev was obtained by PCR using pSA212 as a template and using primers 1F (SEQ ID NO: 1) and 1R (SEQ ID NO: 2). The DNA fragment having an EcoRI site at the 3' end thereof was prepared by designing the PCR primer to contain EcoRI restriction enzyme site. After digested with BglII and EcoRI, the PCR fragment was purified by agarose gel electrophoresis and Wizard PCR Preps DNA Purification System (Promega). The DNA fragment resulting from the above procedure, together with a DNA fragment encoding the gag/pol region (containing the region from the XhoI site (356) to the BglII site (5338)), were ligated at the XhoI-EcoRI site in pBluescript KS+ (Stratagene). Then, PCR amplification was performed for a DNA fragment corresponding to the region containing Rev responsive element (RRE) and the second exon (6964–7993) of tat/rev. In a similar manner as described above for the PCR fragment, PCR was carried out using pSA212 as a template and using primers 2F (SEQ ID NO: 3) and 2R (SEQ ID NO: 4) for addition of a NotI site at the 3' end. After digested with EcoRI and NotI, the DNA fragment was purified and inserted at the EcoRI-NotI site of pBluescript KS+ in which gag-tat/rev had already been inserted.

Further, DNA fragments containing a splicing donor (SD) site were synthesized (sequence 3F (SEQ ID NO: 5) and 3R (SEQ ID NO: 6)). At the synthesis, an XhoI site and a SalI site were integrated at the 5' and 3' ends of the DNAs, respectively, and then the DNA was inserted at the XhoI site in the above pBluescript KS+ inserted gag-RRE-tat/rev. The resulting plasmid was digested with XhoI and NotI, and the fragment containing the region from SD to tat/rev was purified. Then the fragment was inserted at XhoI-NotI site in a plasmid pCAGGS (Gene, vol. 108, pp 193–200, 1991) inserted an XhoI/NotI linker (sequence 4F (SEQ ID NO: 7) and 4R (SEQ ID NO: 8)) already at the EcoRI site. The plasmid obtained via the above method was used as a packaging vector (pCAGGS/SIVagm gag-tat/rev).

b. Generation of Gene Transfer Vector

PCR amplification was conducted using pSA212 as a template and using primers 5-1F (SEQ ID NO: 9) and 5-(1R (SEQ ID NO: 10) for SIVagmTYO1-derived 5'LTR region (8547–9053+1–982, which was added KpnI site at the 5' end and EcoRI site at the 3' end); primers 5-(2F (SEQ ID NO: 11) and 5-(2R (SEQ ID NO: 12) for RRE (7370–7993, which was added EcoRI site at the 5' end and SacII site at the 3' end); or primers 5-( 3F (SEQ ID NO: 13) and 5-(3R (SEQ ID NO: 14) for 3'LTR (8521–9170, which was added NotI and BamHI sites at the 5' end, and SacI site at the 3' end). CMV promoter and EGFP encoding region (1–1330; which was added SacII site at the 5' end, and added NotI site and BamHI site as well as a translational stop codon at the 3' end) derived from pEGFPC2 (Clontech) was amplified by PCR using primers 6F (SEQ ID NO: 15) and 6R (SEQ ID NO: 16), and pEGFPC2 as a template. The four types of PCR fragments were respectively digested with a pair of restriction enzymes of KpnI and EcoRI, a pair of EcoRI and SacII, a pair of BamHI and SacI, and a pair of SacII and BamHI, followed by purification. Then, they were ligated in the order of 5'LTR, 3'LTR, RRE and CMV promoter EGFP prior to the insertion between KpnI-SacI site of pBluescript KS+ (pBS/5'LTR.U3G2/RREc/s/CMVFEGFP/WT3'LTR). When β-galactosidase was used as a reporter gene, the DNA fragments containing the 5'LTR region and 3' LTR region respectively were prepared by PCR as described above. After digestion with a pair of restriction enzymes KpnI and EcoRI and a pair of NotI and SacI respectively, the DNA fragments were purified, and then inserted at the KpnI-EcoRI site and the NotI-SacI site of pBluescript KS+, respectively (pBS/5' LTR.U3G2/WT3' LTR). A NotI fragment containing the region encoding β-galactosidase of pCMV-beta (Clontech) (820–4294) was inserted into the plasmid at the NotI site (pBS/5' LTR.U3G2/beta-gal/WT3' LTR). Then, an RRE sequence (6964–8177; which was added EcoRI site at the 5' end and added NotI site at the 3' end), which had been amplified by PCR using primers 7-1F (SEQ ID NO: 17) and 7-(1R (SEQ ID NO: 18) as well as using pSA212 as a template, was inserted at the EcoRI-NotI site in plasmid pBS/5' LTR.U3G2/beta-gal/WT3' LTR (pBS/5' LTR.U3G2/RRE6/tr/beta-gal/WT3' LTR). The RRE sequence was cut out with EcoRI and NheI prior to the insertion of the RRE sequence (7370–7993; which was added EcoRI site at the 5' end and added NheI site at the 3' end), which had been amplified by PCR using primers 7-(2F (SEQ ID NO: 19) and 7-(2R (SEQ ID NO: 20) as well as using pSA212 as a template. After the resulting plasmid (pBS/5' LTR.U3G2/RREc/s/beta-gal/WT 3' LTR) was digested with NheI and SmaI and blunted, a CMV promoter region (8–592; blunted AseI-NheI fragment) derived from pEGFPN2 (Clontech) was inserted therein (pBS/5' LTR.U3G2/RREc/s/CMVFbeta-gal/WT3' LTR). All blunting reactions were performed using a Blunting High (Toyobo) according to the attached instruction. The plasmids pBS/5' LTR.U3G2/RREc/s/CMVFEGFP/WT3' LTR and pBS/5' LTR.U3G2/RREc/s/CMVFbeta-gal/WT3' LTR were digested with KpnI and SacI respectively to provide DNA fragments containing the region between 5' LTR-3' LTR. The fragments were inserted into pGL3 Control vector (Promega) at the KpnI-SacI site for use as a gene transfer vector (pGL3C/5' LTR.U3G2/RREc/s/CMVFbeta-gal or EGFP/WT3' LTR). For the identification of packaging signal, the 5'LTR region was cut off with KpnI and EcoRI from pBS/5' LTR.U3G2/RREc/s/CMVFbeta-gal/WT3' LTR plasmid, and a variety of DNA fragments were prepared for each containing a region of different length by PCR using a primer 8F (SEQ ID NO: 21) and a series of primers 8-(1R to 12R (SEQ ID NOs: 22–33) as well as using pSA212 as a template. Each of the 12 types of the resulting DNA fragments were inserted at the KpnI-EcoRI site in the plasmid described above. The resulting vectors were used for the identification.

Further, a vector into which a frame shift was introduced in the region encoding gag polypeptide was obtained by inserting a DNA fragment prepared by PCR using 8-FSF (SEQ ID NO: 34) and 8-FSR (SEQ ID NO: 35) and using pSA212 as a template, into EcoRI site of a vector in which a DNA fragment prepared by PCR using primers 8F (SEQ ID NO: 21) and 8-3R (SEQ ID NO: 24) and using pSA212 as a template had been inserted at the KpnI-EcoRI site. A vector into which a point mutation had been introduced at the translation initiation codon (ATG) of the gag polypeptide was obtained by insertion of a DNA fragment prepared by PCR using 8-FSF (SEQ ID NO: 34) and 8-FSR (SEQ ID NO: 35) and using pSA212 as a template, into EcoRI site of a vector in which a DNA fragment prepared by PCR using a primer 8F (SEQ ID NO: 21) and a series of primers 8-PMR1 to 9 (SEQ ID NOs: 36 to 44) and using pSA212 as a template had been inserted at the KpnI-EcoRI site.

A typical method for verifying the performance of vectors is described as follows. 293T cells are plated on a 6-well plastic plate (Sumitomo Bakelite) at a cell density of $5 \times 10^5$ per well and then cultured in a $CO_2$ incubator (at 37° C. in an atmosphere of 10% $CO_2$ gas) for 48 hours. After the cultivation, the culture medium is changed to 800 μl/well of OptiMEM for transfection. The amounts of DNA to be used per well are 300 ng for gene transfer vector, 600 ng of packaging vector and 100 ng of VSV-G expression vector (pHCMV-G, Methods in Cell Biology, vol. 43, pp 99–112, 1994). The DNAs are dissolved in 100 μl of OptiMEM and then 6 μl of PLUS reagent is added thereto. After the mixture is stirred and allowed to stand at room temperature for 15 minutes, a 4 μl aliquot of LIPOFECTAMINE diluted with 100 μl of OptiMEM is added to the mixture, followed by the further stirring and placement at room temperature for another 15 minutes. The resulting solution containing the complex of DNA and LIPOFECTAMINE prepared by the above method is instilled to 293T cells cultured in wells of a 6-well plate and stirred gently, followed by cultivation in a $CO_2$ incubator (at 37° C. in an atmosphere of 10% $CO_2$ gas) for 3 hours. After the incubation, 1 ml/well of D-MEM containing 20% inactivated fetal bovine serum is added to the mixture, and then cultivated in an atmosphere of 10% $CO_2$ gas in a $CO_2$ incubator at 37° C. for 12 hours. Then, the medium of the mixture is changed to 2 ml/well of D-MEM containing 10% inactivated fetal bovine serum, followed by the cultivation for 24 hours. The supernatants of cell culture are filtered with a filter of pore size of 0.45 μm (DISMIC-25CS filter; ADVANTEC) for the assay.

In the case of the preparation of a concentrated stock, 293T cells are first plated on a 15-cm plastic plate (Sumitomo Bakelite) at a cell density of $2.5 \times 10^6$ cells per well followed by cultivation in a $CO_2$ incubator (at 37° C. in an atmosphere of 10% $CO_2$ gas) for 48 hours. Then, the culture medium is changed to 10 ml/well of OptiMEM for the transfection. The DNAs to be used per well are 6 μg gene transfer vector, 3 μg packaging vector, and 1 μg VSV-G expression vector (pHCMV-G). After the DNAs are dissolved in 1.5 ml of OptiMEM, 40 μl PLUS reagent is added thereto, and then stirred and allowed to stand still at room temperature for 15 minutes. A 60 μl aliquot of LIPOFECTAMINE diluted with 1 ml of OptiMEM was added to the mixture, followed by stirring and placement at room temperature for another 15 minutes. The solution containing the complex of DNA and LIPOFECTAMINE prepared by the above method is instilled to 293T cells cultured in wells of 6-well plate and stirred gently, followed by the cultivation in an atmosphere of 10% $CO_2$ gas in a $CO_2$ incubator at 37° C. for 3 hours. After the incubation, 10 ml/plate of D-MEM containing 20% inactivated fetal bovine serum is added to the mixture, and then incubated in an atmosphere of 10% $CO_2$ gas in a $CO_2$ incubator at 37° C. for 12 hours. Then, the medium of the mixture is changed to 20 ml/plate of D-MEM containing 10% bovine fetal serum, followed by the further cultivation for 24 hours. The supernatants of cell culture are filtered with a filter of pore size of 0.45 μm and concentrated to 100 times by ultrafiltration through centrifugation in a Centriplus YM-100 (Amicon) at 4° C. at 3000 g for 170 minutes. The concentrated sample is stored at −80° C. to use for the assay.

The efficiency of gene transfer for the SIVagm virus vector prepared above can be determined using the human 293T cell line, etc. In addition, the efficiency of gene transfer in a particular phase of cells cycle can be evaluated by aphidicolin treatment (arrest at G1-S phase) or X-ray irradiation (arrest at G2-M phase) as described below.

Further, it is possible to determine whether or not the SIVagm vector can be introduced into cells in a state closer to a physiological one, when the introduction experiment is conducted by using a variety of cells. Such cells include, for example, the cells in which differentiation is induced by the treatment of human neuroblast cell line RBTM1 and SH-SY5Y with all-trans retinoic acid, and primary culture of rat brain cells (infra), etc.

EXAMPLE 2

Modification of 5'LTR

Figure 2:
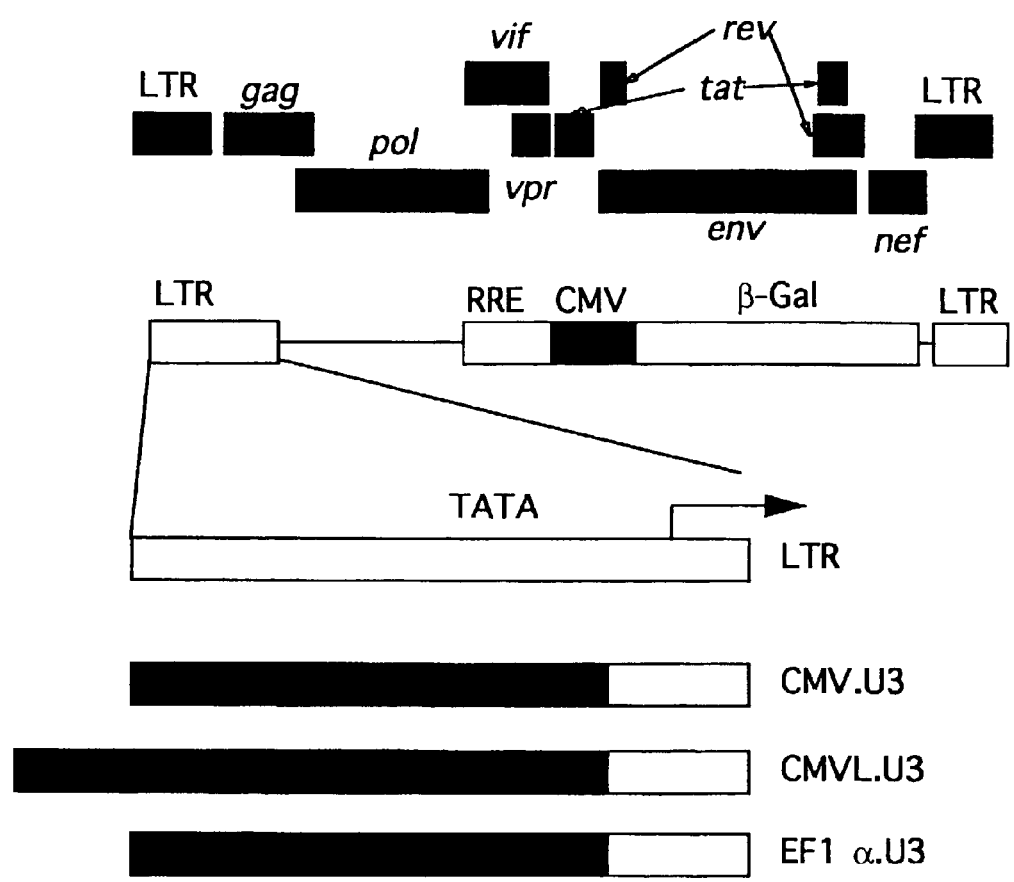

The transcriptional activity of 5'LTR from lentivirus is generally depends on the presence of Tat protein, which is a virus-derived factor. Thus, to eliminate the Tat dependence as well as to enhance the vector titer by the replacement with a promoter sequence having stronger transcriptional activity, an SIVagm gene transfer vector was generated, in which the U3 region that is a promoter sequence of the 5'LTR was replaced with another promoter sequence (FIG. 2).

The replacement of the 5'LTR with a chimeric promoter was achieved as follows. A fragment containing a region between downstream of TATA box on the 5'LTR to the gag region (9039–9170+1–982) was amplified by PCR using a series of primers 9-1F to 3F (SEQ ID NOs: 45–47) and a primer 9R (SEQ ID NO: 48) as well as using pSA212 as a template. Further, fragments each containing CMVL promoter (derived from pCI (Promega); 1–721), CMV promoter (derived from pEGFPN2 (Clontech); 1–568), EF1α promoter (nucleotides 2240–2740 from pEF-BOS (Nucleic Acids Research, vol. 18, p5322, 1990)), and CA promoter (nucleotides 5–650 from pCAGGS) were amplified by PCR, respectively, using a pair of primers 10-1F (SEQ ID NO: 49) and 10-1R (SEQ ID NO: 50) as well as using pCI as a template; a pair of primers 10-2F (SEQ ID NO: 51) and 10-2R (SEQ ID NO: 52) as well as using pEGFPN2 as a template; a pair of primers 10-3F (SEQ ID NO: 53) and 10-3R(SEQ ID NO: 54) as well as using pEF-BOS as a template; and a pair of primers 10-4F (SEQ ID NO: 55) and 10-4R(SEQ ID NO: 56) as well as using pCAGGS as a template. After the amplification, the fragment containing 5'LTR was mixed with each of the above fragments containing each promoters. The primer (10-1F (SEQ ID NO: 49), 10-2F (SEQ ID NO: 51), 10-3F (SEQ ID NO: 53), or 10-4F (SEQ ID NO: 55)) corresponding to the 5' end of each promoter and the primer corresponding to the 3' end of 5'LTR (9R) were added thereto, and then, PCR was performed with another 10 cycles to obtain DNA fragments of chimeric promoter consisting of each of the four types of promoters and 5'LTR. The resulting DNA fragments were inserted into a gene transfer vector (pGL3C/5' LTR.U3G2/RREc/s/CMVFbeta-gal/WT3' LTR) at the KpnI-EcoRI site (pGL3C/CMVL.U3G2/RREc/s/CMVFbeta-gal/WT3' LTR, pGL3C/CMV.U3G2/RREc/s/CMVFbeta-gal/WT3' LTR, pGL3C/EF1α. U3G2/RREc/s/CMVFbeta-gal/WT3' LTR, pGL3C/CAG.U3G2/RREc/s/CMVFbeta-gal/WT3' LTR).

EXAMPLE 3

Modification of 3'LTR

Figure 3:
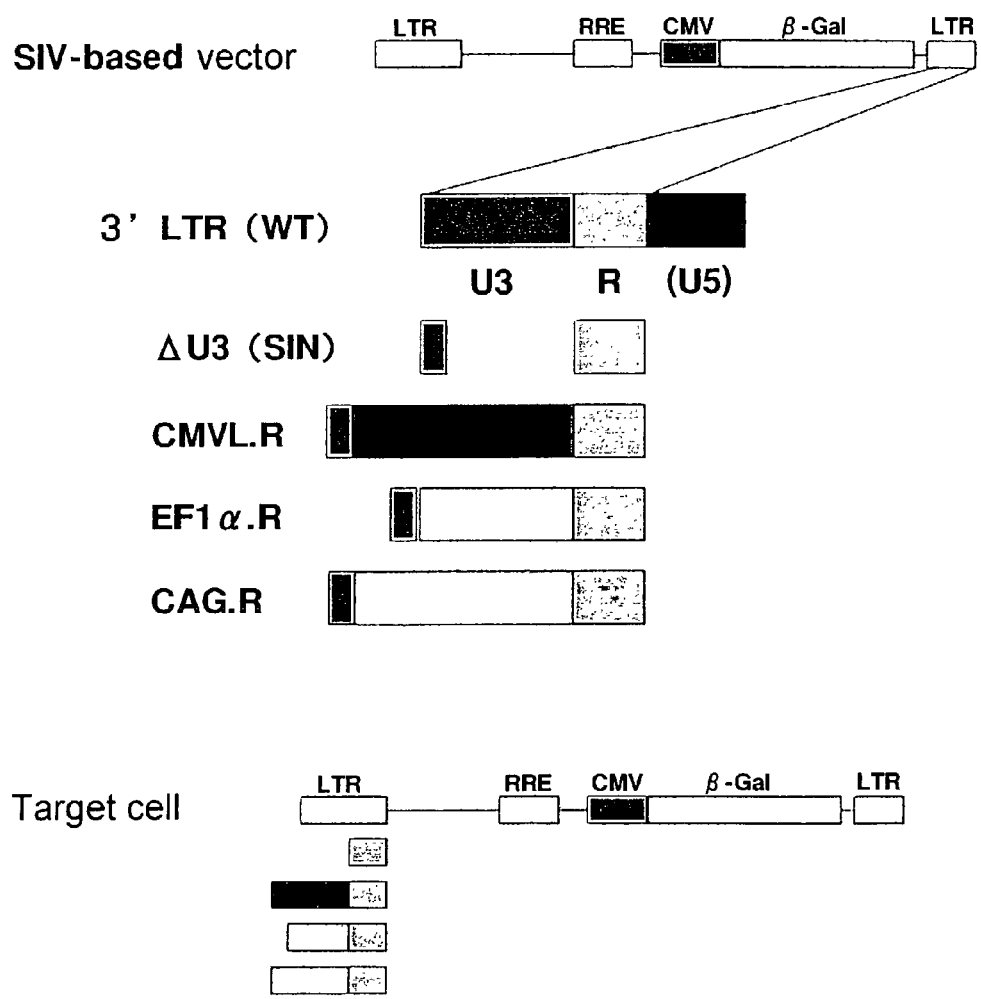

In a lentivirus vector, as the U3 region, a promoter sequence, which is contained in the 3'LTR region, is integrated in the U3 promoter region of 5'LTR at the time of reverse transcription in target cells. It is found that the U3 region contained in the 3'LTR region of a gene transfer vector plasmid becomes the U3 promoter in 5'LTR participating in gene expression in the genome of target cells (FIG. 3). Thus, SIVagm gene transfer vectors were prepared, in which the U3 region of 3' LTR was replaced with other promoter sequences that may be evaluated to determine whether or not the promoter, which relates in gene expression in target cells, can be replaced with other promoters other than the U3 sequence (FIG. 3). In addition, SIVagm gene transfer vectors were prepared, in which the U3 region of 3' LTR was deleted, which may be evaluated to determine whether or not the promoter sequence on the 5'LTR in target cells can be deleted.

The modification and deletion of the U3 promoter sequence of 3'LTR was achieved as follows. A DNA fragment without U3 of 3'LTR was amplified by PCR using primers 11F (SEQ ID NO: 57) and 11R (SEQ ID NO: 58) and using pSA212 as a template. Further, 3'LTRs, in which the U3 region had been replaced with other promoters, were amplified by PCR using a series of primers 12-1F to 3F (SEQ ID NOs: 59–61) and a primer 12R (SEQ ID NO: 62) as well as using, as a template, each of vector plasmids, in which the chimeric promoter obtained by the method as described in Example 2 had been inserted, pGL3C/CMVL.U3G2/RREc/s/CMVFbeta-gal/WT3' LTR, pGL3C/EF1α. U3G2/RREc/s/CMVFbeta-gal/WT3' LTR, and pGL3C/CAG.U3G2/RREc/s/CMVFbeta-gal/WT3' LTR. The resulting DNA fragments provided by PCR were digested with SalI and SacI, purified, and inserted into pGL3C/CMVL.U3G2/RREc/s/CMVFbeta-gal/WT3' LTR at the SalI-SacI site (pGL3C/CMVL.U3G2/RREc/s/CMVFbeta-gal/3LTRdeltaU3, pGL3C/CMVL.U3G2/RREc/s/CMVFbeta-gal/CMVL.R, pGL3C/CMVL.U3G2/RREc/s/CMVFbeta-gal/EF1α. R, and pGL3C/CMVL.U3G2/RREc/s/CMVFbeta-gal/CAG.R), respectively.

EXAMPLE 4

Identification of Packaging Signal

Figure 4:
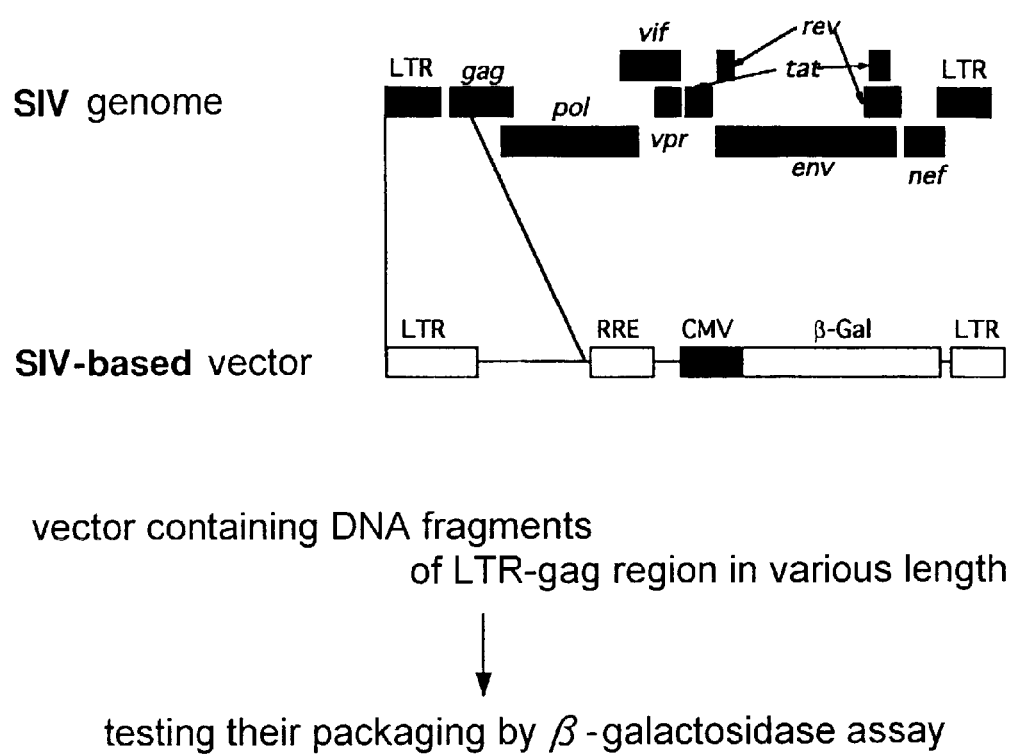

Packaging of a gene transfer vector into vector particles requires a packaging signal that is a cis-acting element on the gene transfer vector and a trans-acting protein produced by the packaging vector. Since enhancement of packaging efficiency of the vector can be predicted to cause the enhancement of its titer, it is necessary to insert into the vector as a long region comprising the packaging signal as possible so as to keep the structure formed by the packaging signal sequence. On the other hand, probability of the generation of wild-type virus, which may be caused by the recombination between sequence of packaging signal of the gene transfer vector and packaging vector, can be minimized by minimizing the overlap between them. Thus, it is necessary to identify the minimal region required for the packaging. Accordingly, the accurate identification of the minimal packaging signal sequence is necessary for the efficient packaging of gene transfer vector to construct the vector system. Such identification of packaging signal can be achieved by the method as shown in FIG. 4.

Figure 5:
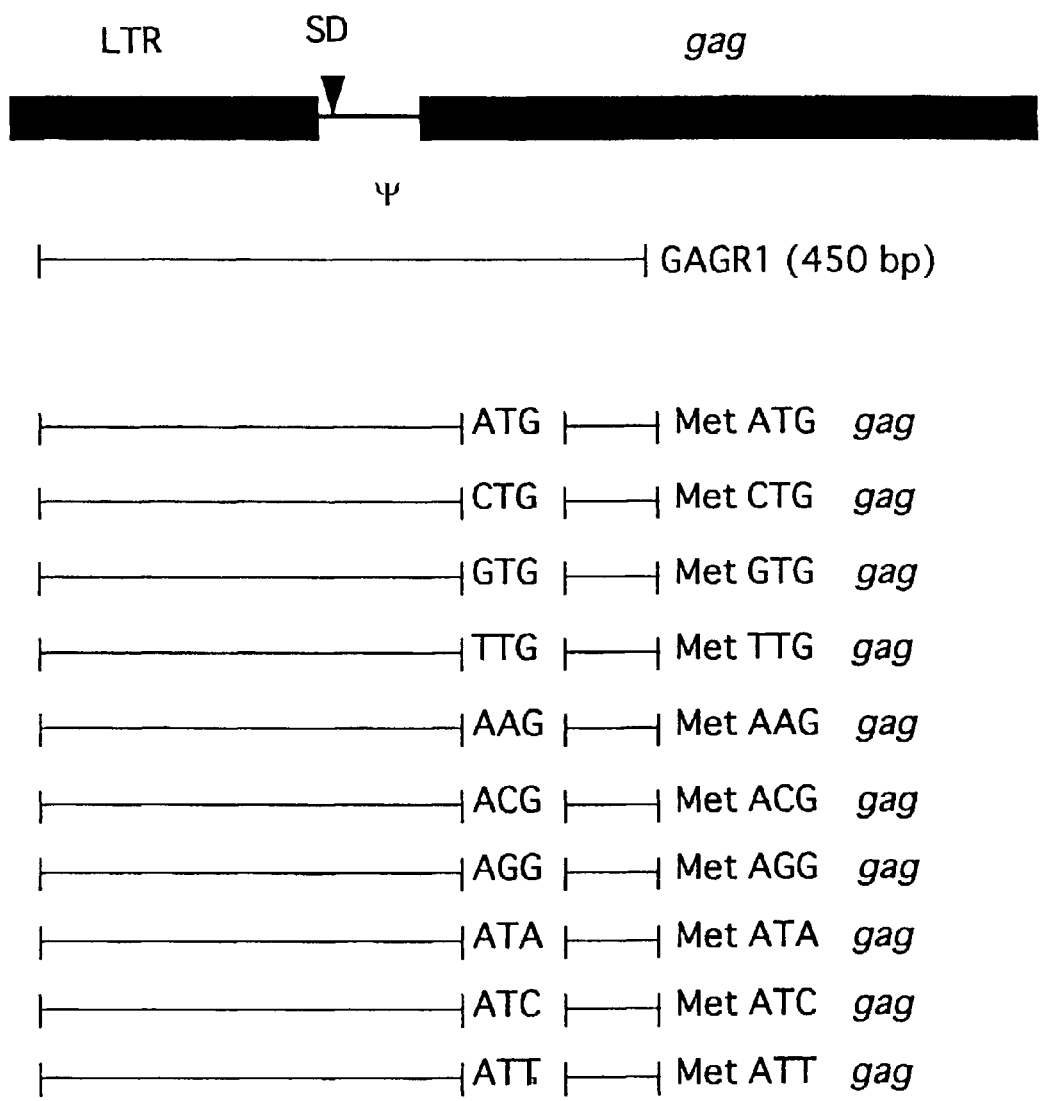

Whether the polypeptide expressed from the gag region or the DNA sequence per se in the gag region is required for the packaging may be explained by comparing the packaging efficiency of gene transfer vector into which mutations as shown in FIG. 5 were introduced, with that of wild-type gene transfer vector.

EXAMPLE 5

Development of Novel Two-Gene Coexpression System

Rev responsive element (RRE) is a binding site for the virus-derived Rev protein and is associated with the transfer of RNA from the nucleus to cytoplasm. We evaluated whether a system for the simultaneous expression of two different proteins promoted by a single promoter can be constructed by regulating the splicing efficiency using the RRE/Rev system.

Figure 6:
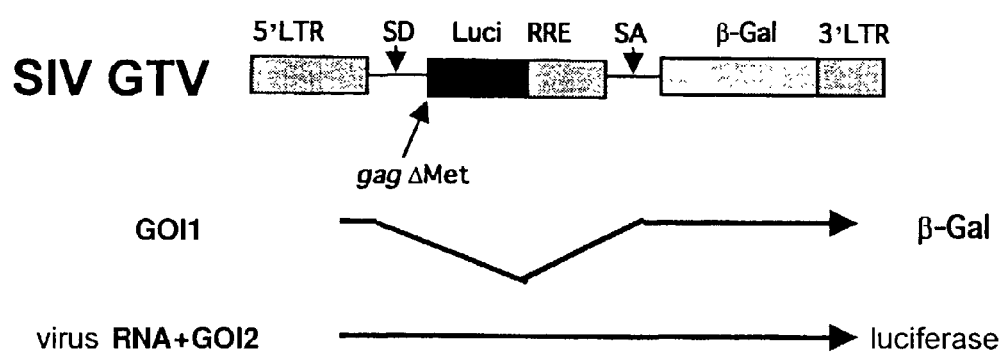

First, for determination whether the expression of two different proteins can be regulated by RRE, a vector was generated as shown in FIG. 6. More specifically, as reporter genes, the luciferase gene and β-galactosidase gene were inserted upstream and downstream of RRE, respectively. Further a splicing donor sequence was inserted upstream of the luciferase gene and a splicing acceptor sequence was inserted downstream of the RRE to construct a vector. As shown in FIG. 6, two types of mRNAs are predicted to be produced from this vector depending on the presence or absence of splicing. In other words, β-galactosidase protein may be produced from the mRNA subjected to the splicing, while luciferase protein may be produced from the unspliced mRNA. In addition, to evaluate whether it is possible not only to express two different genes but also to control the ratio of expression levels between the two genes by modification of RRE sequences, vectors were generated, each of which were inserted of one of the six types of RRE sequences, to determine the expression level of reporter gene in each of the vectors.

The vectors in which two-gene expression system were inserted and those for the test of the activity of RRE sequence were generated as follows. A DNA fragment in which EcoRI sites were added to both 5' and 3' ends of a gene fragment encoding luciferase was amplified by PCR using primers 13-1F (SEQ ID NO: 63) and 13-1R (SEQ ID NO: 64) with pSP-luc+ (Promega) as a template. Alternatively, a DNA fragment in which EcoRI sites were added to both 5' and 3' ends of a gene fragment encoding EGFP was amplified by PCR using primers 13-2F (SEQ ID NO: 65) and 13-2R (SEQ ID NO: 66) with pEGFPN2 (Clontech) as a template.

Figure 7:
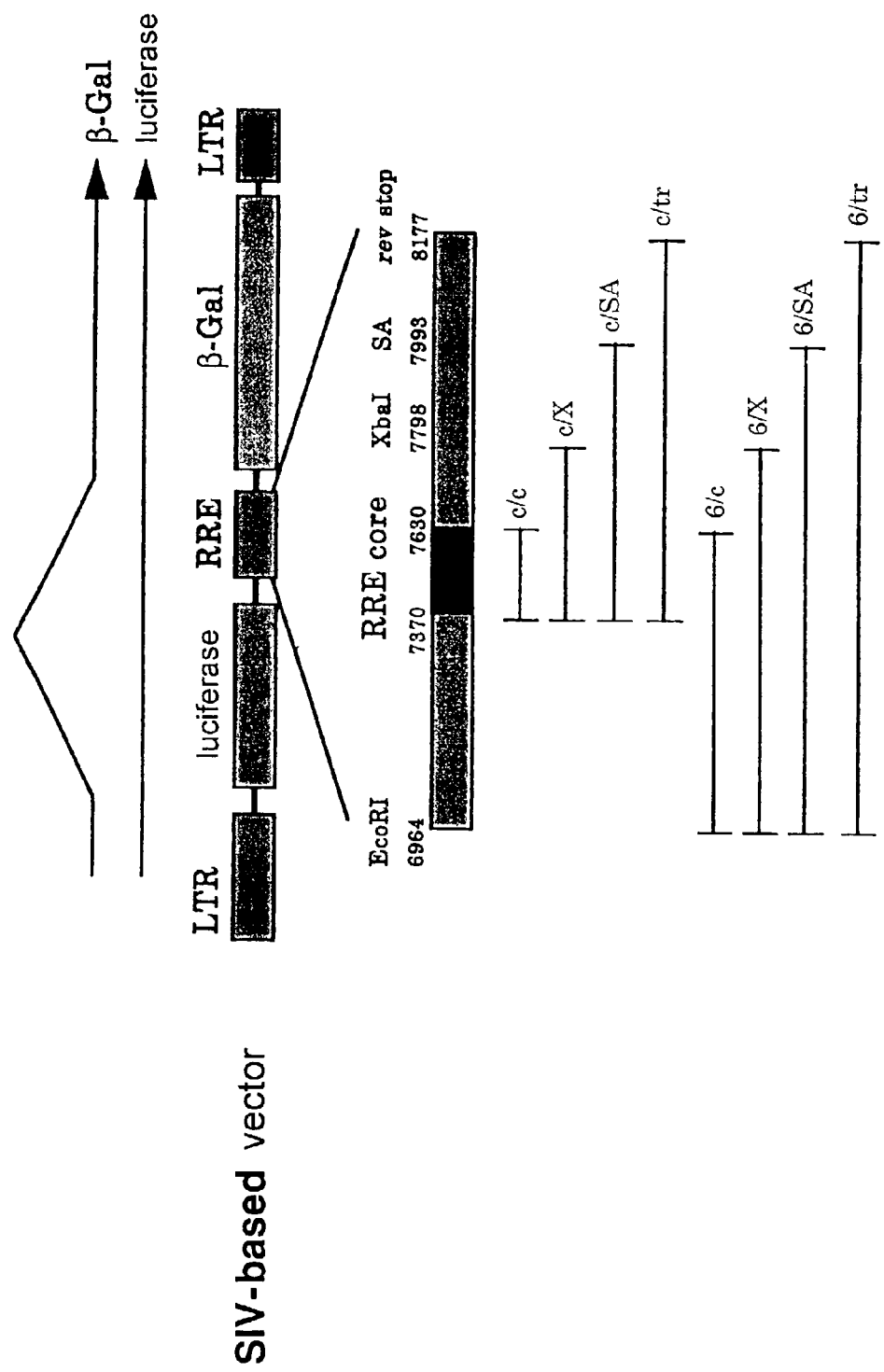

A DNA fragment, containing 5'LTR obtained by PCR using primers 14F (SEQ ID NO: 67) and 14R (SEQ ID NO: 68) and using pSA212 as a template, was inserted into plasmid pBS/5' (pBS/5' LTR.U3Met-/RRE6/tr/beta-gal/WT3' LTR). DNA fragments containing various RRE sequences were obtained by PCR by combining two types of primers, 15-1F (SEQ ID NO: 69) and 15-2F (SEQ ID NO: 70), with three types of primers, 15-1R (SEQ ID NO: 71), 15-2R (SEQ ID NO: 72), and 15-3R (SEQ ID NO: 73)), with pSA212 as a template. Six types of DNA fragments thus obtained were digested with EcoRI and NheI or with EcoRI and XbaI and purified. Each of the six types of purified DNA fragments was substituted for the RRE sequence of plasmid pBS/5' LTR.U3Met-/RRE6/tr/beta-gal/WT3' LTR by digesting the plasmid with EcoRI and NheI to excise the RRE sequence. The gene fragment encoding luciferase or EGFP that had been prepared by the PCR and that had been purified after digested with EcoRI was inserted into the resulting plasmid at the EcoRI site for use in the assay for the activity of RRE sequence (FIG. 7).

The shift of reporter gene through substitution was carried out as follows. Plasmid pBS/5' LTR.U3Met-/RRE6/s/beta-gal/WT3' LTR containing RRE6/s (6964–7993) sequence was digested with NheI and SalI to remove a fragment containing the region encoding β-galactosidase, and then the NheI-XhoI fragment containing the region encoding luciferase (derived from pSP-luc+; 17–1723) was inserted thereto (pBS/5' LTR.U3Met-/RREc/s/luc+/WT3' LTR). Then, a NotI fragment (820–4294) containing the region encoding β-galactosidase from pCMV-beta (Clontech), which was already blunted and then purified, was inserted into pBS/5' LTR.U3Met-/RREc/s/luc+/WT3' LTR, which was already digested with EcoRI and blunted. The resulting plasmid (pBS/5' LTR.U3Met-/beta-gal/RREc/s/luc+/WT3' LTR) was used for the following assay. Both blunting reactions were conducted with a Blunting High (Toyobo) according to the attached instruction.

A DNA fragment of 5'LTR obtained by PCR using a pair of primers 16F (SEQ ID NO: 74) and 16R (SEQ ID NO: 75) as well as using pSA212 as a template was inserted into plasmid pBS/5' LTR.U3Met-/RREc/s/beta-gal/WT3' LTR that has been digested with KpnI and EcoRI (pBS/5' LTR.U3G3/RREc/s/beta-gal/WT3' LTR).

A purified gene fragment encoding EGFP prepared by PCR and then digested with EcoRI, was inserted into pBS/5' LTR.U3G3/RREc/beta-gal/WT3'LTR at the EcoRI site. The resultiong plasmid was digested with KpnI-SacI to prepare a DNA fragment containing 5'LTR-3'LTR to be inserted into pGL3Control vector (Promega) at the KpnI-SacI site. The resulting plasmid was used for the test of the two-gene expression system in situ.

The gene transfer vector obtained as described above was used for the transfection to 293T cells, as follows, to assay β-galactosidase and luciferase activity. As shown in the graph of FIG. 8, the result revealed that the two different genes can be coexpressed from the vector having RRE sequence as well as that the substitution of RRE sequence can regulate the expression efficiency of the two genes. In addition, based on the result that the two different genes were coexpressed in the absence of packaging vector, it was revealed that Rev protein-independent expression of the two genes can be achieved in the present gene expression system.

EXAMPLE 6

Specificity to the Promoter in the Two-Gene Coexpression System

It was tested whether the two-gene coexpression system using RRE may be applied to other expression systems using various types of promoters other than the 5'LTR promoter from SIVagmTYO1 used in the above Example. Other promoters derived from human cytomegalovirus (CMV) or a mammalian cell-derived promoter (EF1α promoter) were used as promoters (lower panel of FIG. 9).

Figure 9:
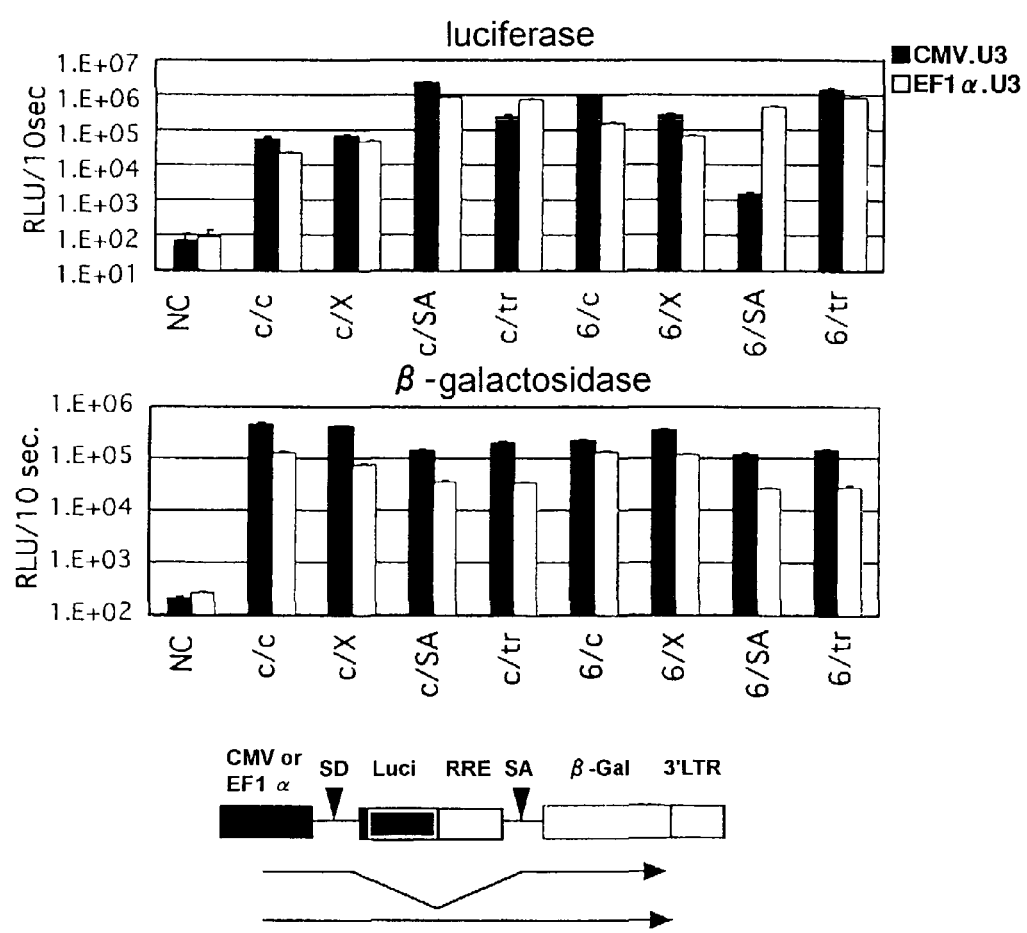

As shown in the graph of FIG. 9, the result indicated that the two-gene coexpression may be achieved using promoters other than 5'LTR. Furthermore, the expression levels of the two genes were found to be regulated depending on the presence of RRE sequence. Thus, this indicates that the two-gene coexpression system using RRE may be widely applied to expression systems using various types of promoters.

EXAMPLE 7

Position Effect of Reporter Gene

Tests were run to determine whether the expression level of each gene varied depending on whether the reporter gene has been inserted upstream or downstream of RRE. Using the SIVagm gene transfer vector, a vector, containing RRE6/s (6964–7993) sequence, was prepared in which the positions of β-galactosidase and luciferase had been changed with each other (lower panel of FIG. 10) to compare. The expression levels between two reporter genes on the two vectors.

Figure 10:
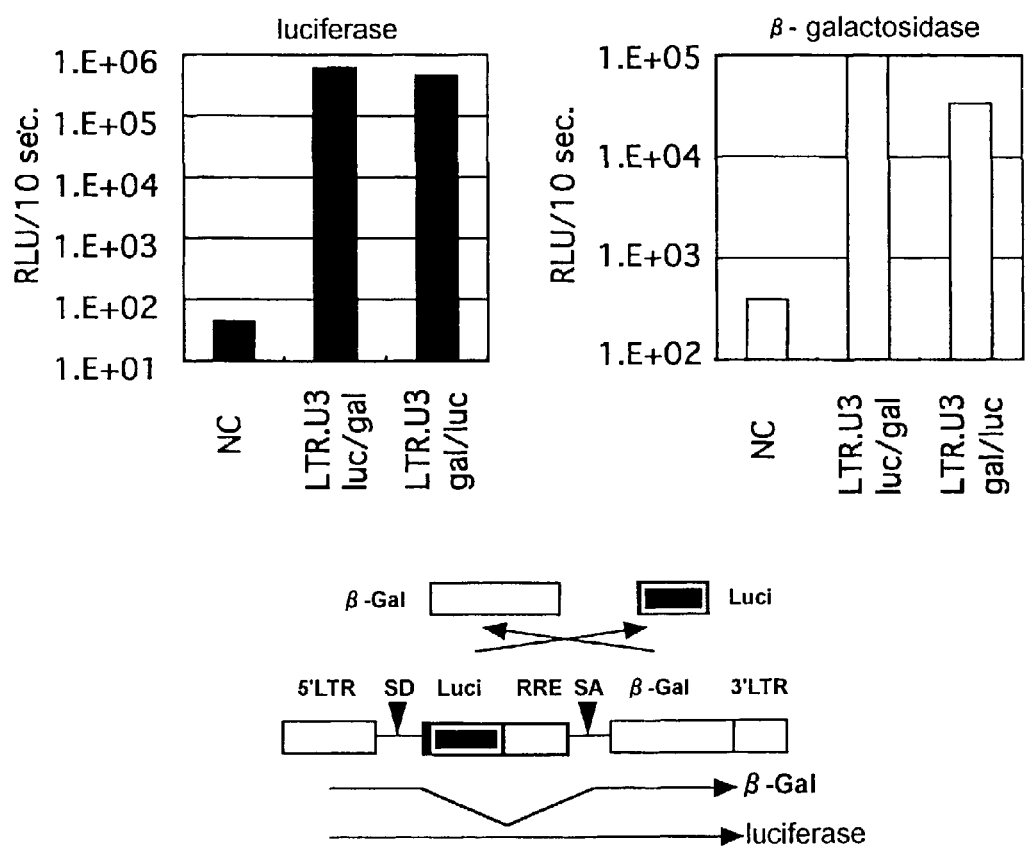

As shown in the graph of FIG. 10, the results indicated no difference in the expression levels of reporter genes, whether the reporter gene had been inserted upstream or downstream of RRE. That is, the two-gene coexpression system using RRE sequence was found to be useful for the expression of proteins which function by forming a complex at a 1:1 molar ratio, particularly, such as various receptors and transcription factors.

EXAMPLE 8

Verification of Performance of SIN Vector (Self Inactivating Vector)

Considering that the gene transfer vector pGL3C/CMVL.U3G2/RREc/s/CMVF β-gal/3' LTRΔU3 prepared in Example 3 lacks the U3 region of 3'LTR, it can be assumed that the safety was enhanced as Self Inactivating Vector (SIN vector), which prevents the transcription of full-length mRNA corresponding the entire vector in target cells.

In order to determine whether gene transfer efficiency may be affected by changing to SIN, the transfection titer of a SIVagm SIN vector to 293T cells was compared to that of a conventional SIVagm vector having wild-type 3' LTR prepared under a same condition. As a result, the transfection titer was 2.4–2.8 TU/ml for the conventional type and 2.5–2.9 TU/ml for the SIVagm SIN vector. That is, the transfection titer of SIVagm SIN vector was 105% when that of the conventional type was taken as 100%.

Figure 11:
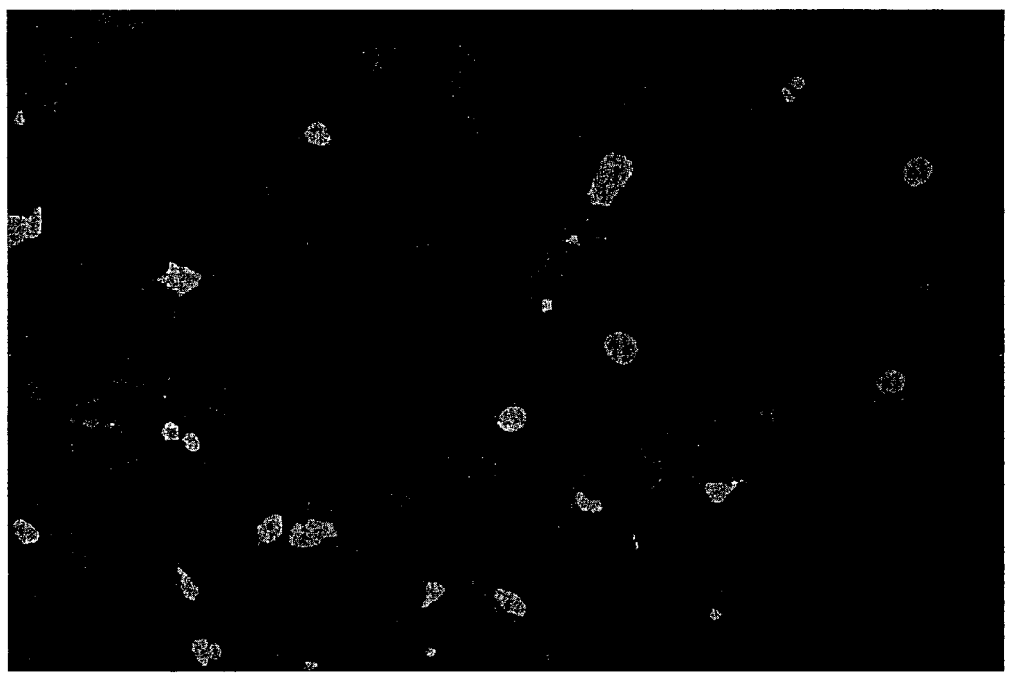
Figure 11:
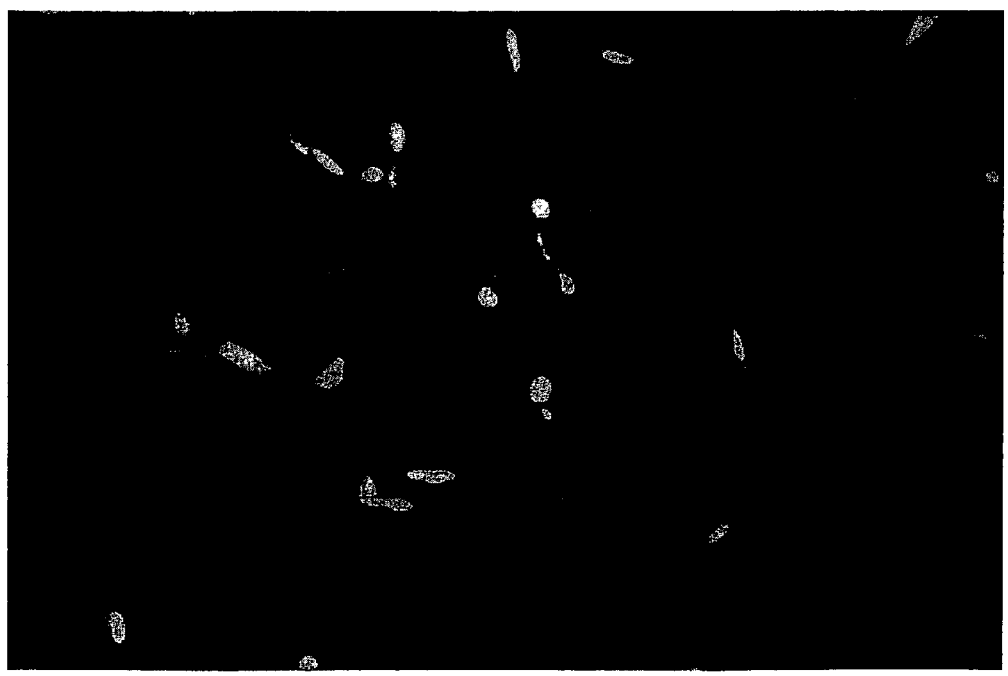

Further, an experiment was conducted in order to achieve SIVagm SIN vector-mediated transfection of the EGFP gene into cell cycle-arrested 293T cells by irradiation and terminal differentiation-induced SH-SY5Y cells by retinoic acid. Observation of the expression of EGFP in the cell cycle-arrested 293T cells with a fluorescence microscope showed that the gene was expressed in high efficiency (upper panel of FIG. 11). Further, EGFP was verified to be expressed in cells having extending neurites, assumed to be cells differentiated to neuronal cells, among SH-SY5Y cells (bottom panel of FIG. 11).

As described above, the efficiency of gene transfer showed to be reduced by the change to SIN.

EXAMPLE 9

SIVagm SIN Vector-Mediated Gene Transfer to Peripheral Blood Lymphocytes and CD34 Positive Cells CD34 positive cells have recently focused on as a fraction containing hematopoietic stem cells (Blood, vol. 87, pp 1–13, 1996). Thus, once it becomes possible to transfer genes into CD34 positive cells, genes can be introduced into hematopoietic stem cells, as well as all types of blood cells differentiated therefrom. Thus, an experiment was conducted to assess the possibility of SIVagm SIN vector-mediated gene transfer into human Peripheral Blood Mononuclear Cells (PBMC), human T cells, human bone marrow-derived and umbilical blood-derived CD34 positive cells, and CD34 positive cells derived from bone marrow of cynomolgus monkey.

The separation of PBMC was conducted by collecting 10 ml of human peripheral blood into a syringe with 200 $\mu$l of 0.5M EDTA for use a Lymphoprep Tube (Nycomed) according to the attached instruction. The separated cells were plated on a 96-well plastic culture plate at a cell density of 2–2.5×10$^5$/well and then cultured in RPMI 1640 medium (Gibco BRL; containing 5% inactivated bovine serum) at 37° C. in an atmosphere of 5% $CO_2$. The induction of the separated PBMCs to T cells was achieved by culturing them in RPMI 1640 containing 5% FCS and 5 mg/ml PHA (SIGMA) for 3 days, adding 40 U/ml IL2 (SHIONOGI&CO) thereto, and further culturing for another 3 days (Current Protocols in Immunology: 6.16.4). For human bone marrow-derived or umbilical blood-derived CD34 positive cells, the frozen cells purchased from Pure-Cell Co. were thawed according to the attached instruction and plated on a 96-well plastic culture plate at a cell density of 2–2.5×10$^5$/well, followed by cultivation in IMDM (Gibco BRL) containing 10% BIT9500 (StemCell). CD34 positive cells derived from bone marrow of cynomolgus monkey (3–7-year old males; averaged body weight=3.0 kg) were plated on a 96-well plastic culture plate at a cell density of 2–2.5×10$^5$/well, followed by cultivation in a (−)MEM (SIGMA) containing 10% inactivated bovine serum (INTERGEN company; REHATUIN®premium grade Lot. RB51901).

The vector-mediated gene transfer was conducted as follows. First, an aliquot of supernatant was removed from the culture medium, and vector pGL3C/CMVL.U3G2/RREc/s/CMVF EGFP/3' LTRΔU3 (titer=1–7×10$^9$ TU/ml) concentrated by a method as describe in Example 1 was layered thereon to be 50 $\mu$l of total volume. Then, the PBMCs were centrifuged at 200 G at 32° C. for 30 minutes and cultured at 37° C. in an atmosphere 5% $CO_2$ for 3 hours. 200 $\mu$l of culture medium was layered thereon and the mixture were cultured for 48 hours. For the CD34 positive cells, without centrifugation after piling up the vector, the cells were then cultured at 37° C. in an atmosphere of 5% $CO_2$ for 3 hours and 200 $\mu$l of culture medium was layered thereon. The mixture were cultured for 48 hours.

The transfer of the EGFP gene was verified by flow cytometry. First, cultured cells were collected from culture wells and washed with PBS containing 3% FCS and 0.05% $NaN_3$. Then, surface antigens of the cells were stained with PE (phycoerythrin)-labeled anti-CD3 antibody, PE-labeled anti-CD14 antibody, and PE-labeled anti-CD19 antibody (Becton Dickinson) according to the attached instruction. After staining, the cells were washed and then fixed with PBS containing 1% PFA for analysis by low cytometer.

Figure 12:
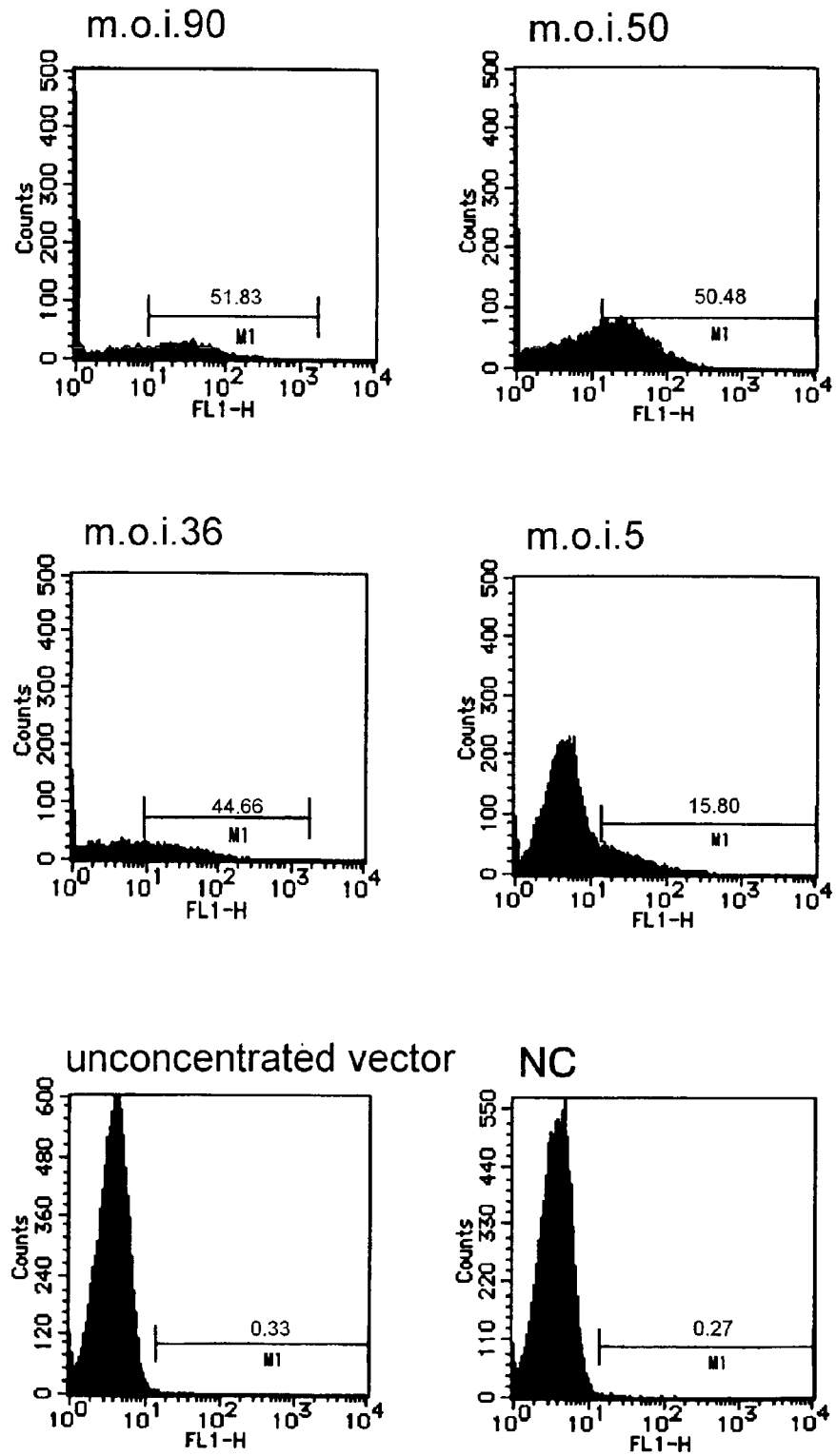
Figure 13:
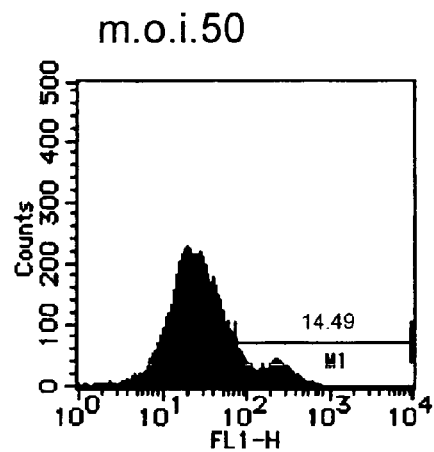
Figure 13:
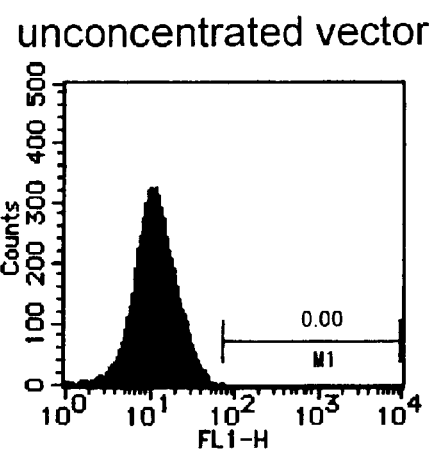
Figure 13:
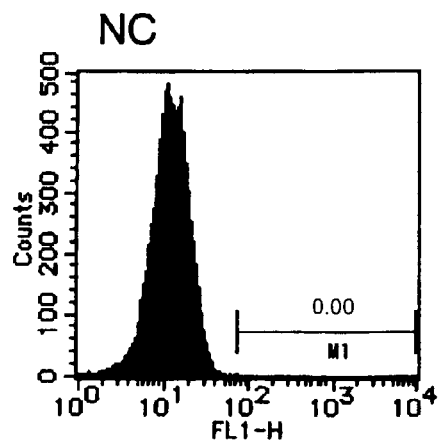
Figure 14:
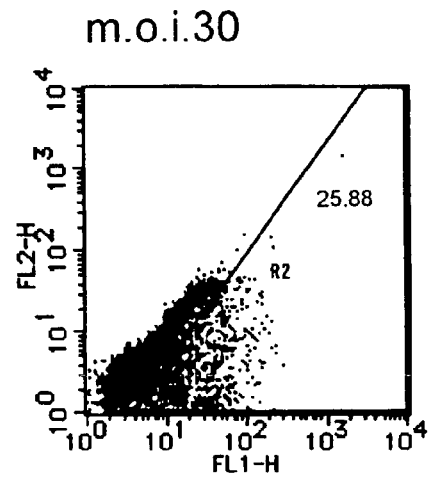
Figure 14:
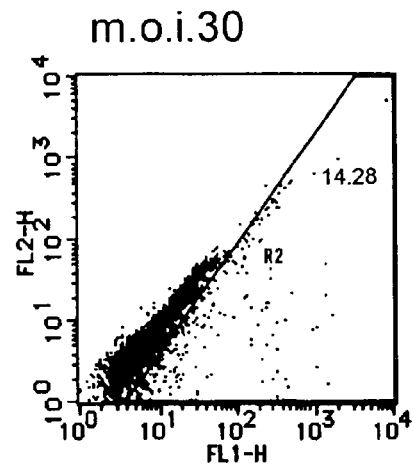
Figure 14:
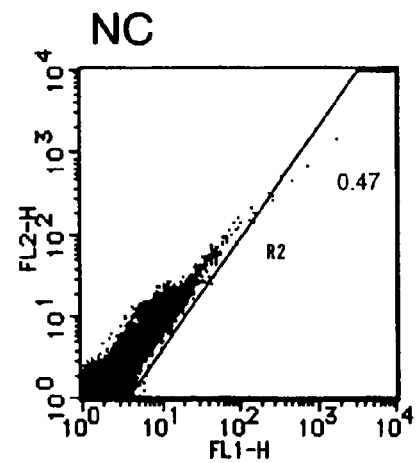
Figure 15:
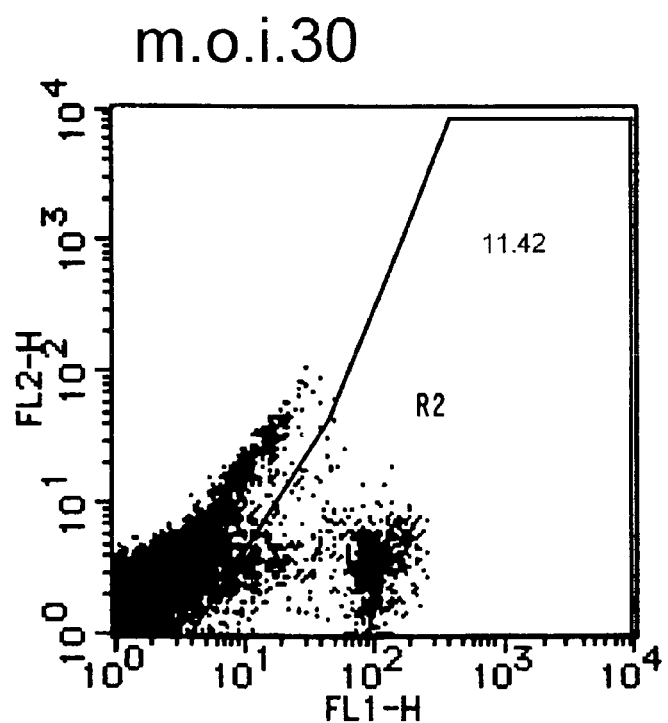
Figure 15:
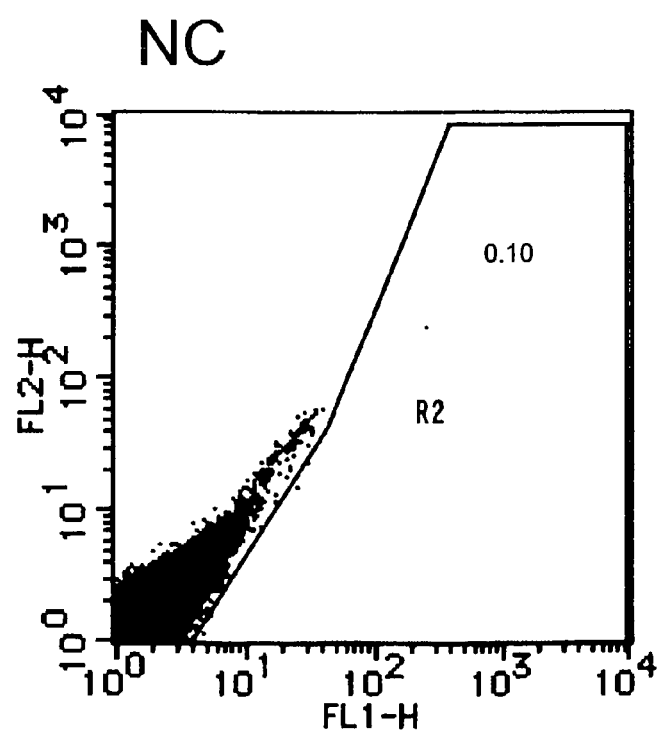
Figure 16:
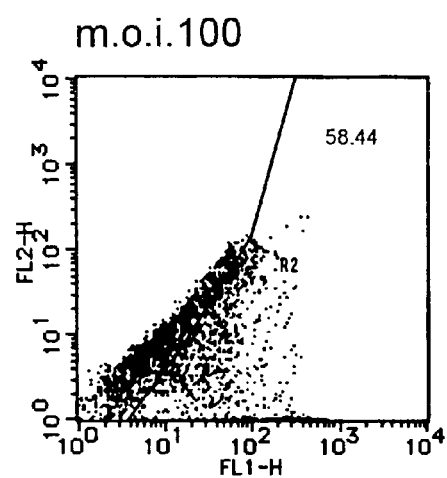
Figure 16:
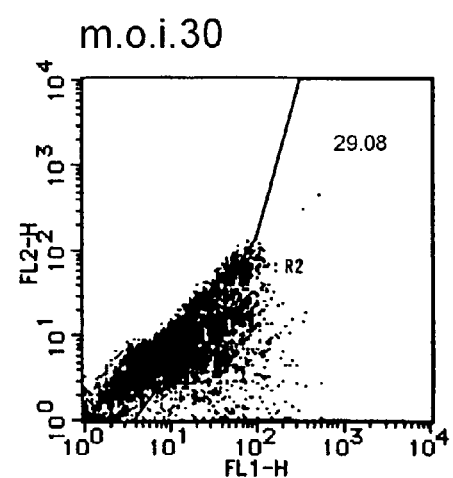
Figure 16:
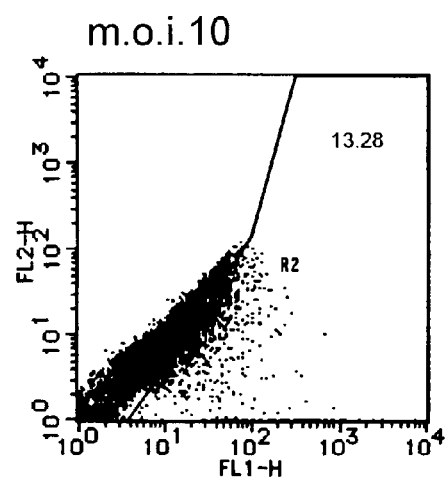
Figure 16:
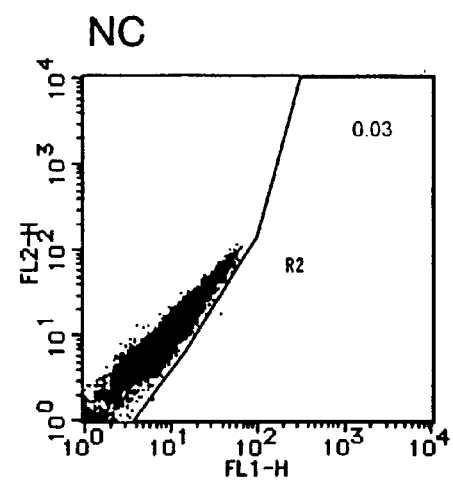

The results showed that 51.8% of the human PBMCs were EGFP positive at 90 of m.o.i. While the percentage of EGFP-expressing cells increased depending on m.o.i., the percentage of EGFP-positive cells was 45% at 36 of m.o.i. and the percentage was not elevated more than about 50% even at m.o.i. higher than that. In addition, no gene transfer was recognized with non-concentrated vector (FIG. 12). For T cells induced from human PBMC, in the analysis 48 hours after the vector infection, the expression of EGFP was recognized in 14.5% of the cells at 50 of m.o.i., but no gene transfer was recognized with non-concentrated vector (FIG. 13). When gene transfer was conducted by using human bone marrow-derived or umbilical blood-derived CD34 positive cells at a m.o.i. of 30, EGFP was expressed in 26% of the bone marrow cells (FIG. 14) or in 11% of the umbilical blood cells (FIG. 15). The increased transfer efficiency in monkey bone marrow-derived CD34 positive cells depending on m.o.i. was found, and the percentage of EGFP expression was 58% at a m.o.i. of 100 (FIG. 16).

The above-mentioned results show that SIVagm SIN vector can mediate gene transfer into PBMCs, T cells, and bone marrow-derived, and umbilical blood-derived CD34 positive cells in high efficiency.

EXAMPLE 10

Reconstitution of Hematopoietic System Using CD34 Positive Cells Subjected to SIVagm SIN Vector-Mediated Gene Transfer The strain of NOD/SCID mouse was produced by back crossing of NOD/Lt mouse, which is IDDM (Insulin Dependent Diabetes Mellitus) mouse, and SCID mouse, which is immunodeficiency mouse, and is a combined immunodeficiency mouse having decreased activity of NK cells, macrophages, and complements, as well as having both T-cell and B-cell defect derived from SCID mouse (J. Immunol., vol. 154, pp 180–191, 1995). NOD/Shi-scid Jic mice (6-week old males), which belong to this line of animal, were purchased from Clea Japan and after 2-week breeding they were used in the experiments.

When human cells with pluripotency are transplanted into an NOD/SCID mouse, hematopoietic system is reconstituted and thus human blood cells will circulate in the mouse body (Nat. Med., vol. 2, pp 1329–1337, 1996). This system was used to evaluate the reconstitution of hematopoietic system due to CD34 positive cells after gene transfer and also to evaluate the expression of EGFP in blood cells thereafter (SCID re-populating cell assay).

First, 8-week old male NOD/SCID mice were exposed to irradiation at a half lethal dose (300 rad). The irradiation was conducted by using Hitachi MBR-1520R under a condition of 150 kv of tube voltage, 20 mA of tube current, 0.5 Al, and 0.1 Cu filter. Within several hours after the irradiation, the cells were injected by a Myjector (Terumo 29Gx1/2" syringe with a needle) at the tail vein with the transplantation.

The cells used for the transplantation were human umbilical blood-derived CD34 cells (PureCell). Cell culture and SIVagm SIN vector-mediated gene transfer were conducted by the same methods as described in Example 9. The infection was performed at 100 of m.o.i. The cells were cultured for 6 hours after vector infection, harvested, washed with IMDM (Gibco BRL), and suspended in IMDM at a cell density of 1–3×10⁶/ml. 1×10⁵ of resulting cells/100 µl per animal were used for the transplantation.

After being transplanted, the animals were bred aseptically in a safety cabinet in a P3 experimental facility. The experiment was conducted using 4 groups of mice; each group contained 10 mice. 28 mice were subjected to the transplantation of cells containing transferred genes; 6 mice were subjected to the transplantation of untreated cells; and the remaining 6 mice were not subjected to the transplantation, followed by breeding of all the mice. Of the 40 animals in total, 25 survived six weeks after the transplantation, indicating 60% of the survival rate. The human cells were taken in five individuals out of the survived individuals, comprising two animals subjected to the transplantation of cells containing transferred genes and three animals subjected to the transplantation of untreated cells.

The peripheral blood was collected 4–6 weeks after the transplantation. After the tail vein was cut by a razor, 50–100 µl of peripheral blood was collected and mixed with 10 µl of 0.5M EDTA to prevent coagulation. 700 µl of distilled water was added to the collected blood and pipetted several times to lyse the erythrocytes. 700 µl of 2×PBS was further added to the mixture, mixed, and then centrifuged (at 5000 rpm for one minute) to recover the total leukocytes in peripheral blood. The recovered leukocytes were suspended in 50 µl of PBS containing 3% FCS and 0.05% NaN₃, and 2 µl of PE-labeled anti-human CD45 antibody (Coulter) was added thereto. The mixture was incubated on ice for 30 minutes, washed twice with PBS containing 3% FCS and 0.05% NaN₃, fixed with PBS containing 1% PFA for analysis by flow cytometry. The analysis was conducted with two colors to detect human CD45-positive cells among mouse leukocytes and also to detect EGFP-expressing cells therein.

Figure 17:
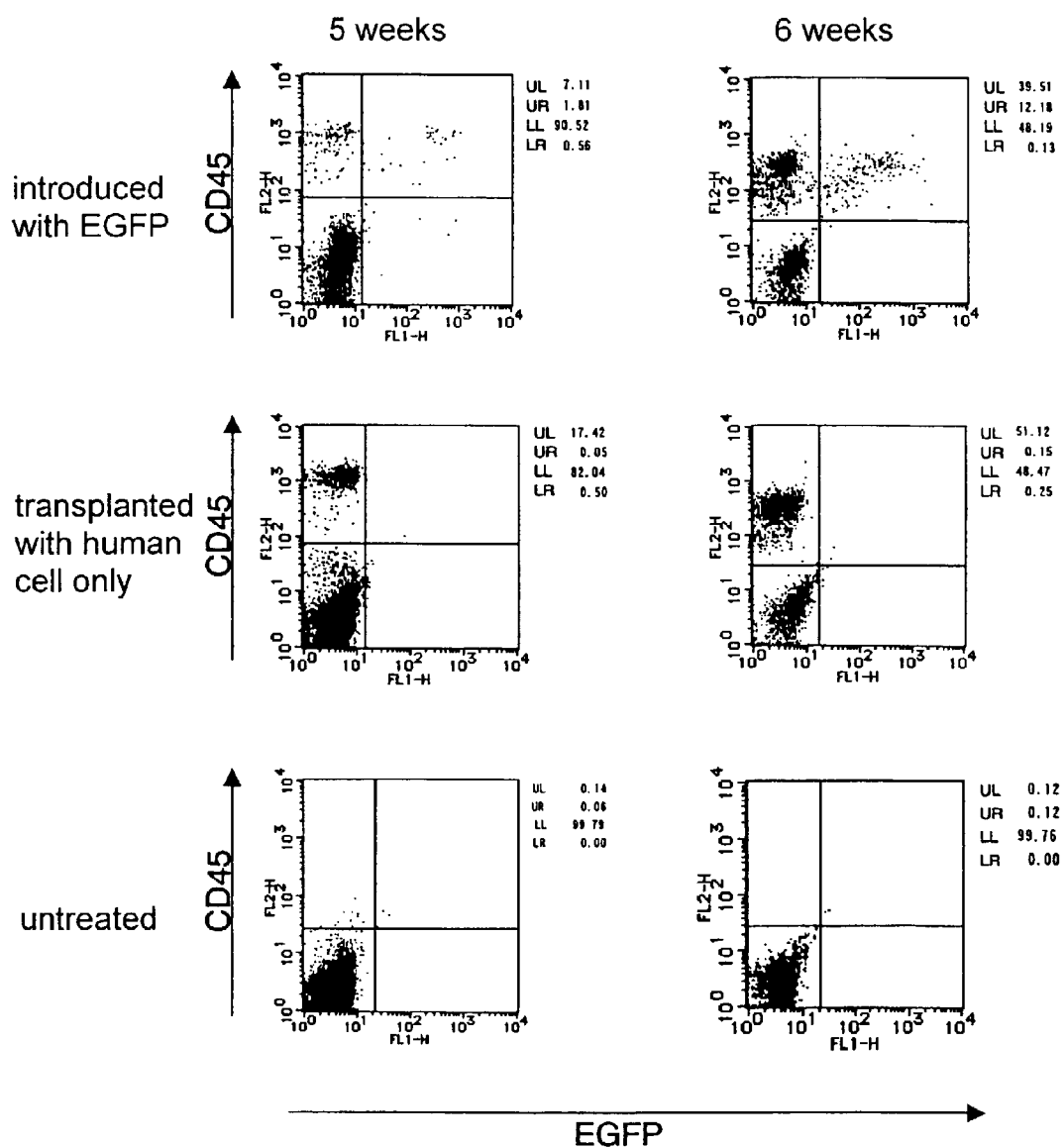

The results showed that human CD45 was expressed in 10–50% cells of leukocytes of peripheral blood from mice in which the human CD34 positive cells had been transplanted. The expression of EGFP was recognized in 20% of human CD45-positive cells among peripheral blood leukocytes from mice subjected to the transplantation of human CD34 positive cells into which the EGFP gene had been introduced by the SIVagm SIN vector (FIG. 17).

[Common Procedures]

Procedures used commonly in this Example are described below in (1)–(7).

(1) Cell Culture 293T cells, human fetal kidney cell-derived cell line (Proc. Natl. Acad. Sci. USA, vol. 90, pp 8392–8396, 1993), were cultured in D-MEM (GibcoBRL) including 10% inactivated fetal bovine serum. The cell cycle is arrested either by treating 293T cells with aphidicolin (Calbiochem; at a final concentration of 20 µg/ml for 48 hours treatment; arrested at G1-S phase) or by irradiating the cells with X-ray (after the irradiation at 200 rad/minute for 20 minutes, the cells were cultured for 48 hours; arrested at G2-M phase). Human cell line of neuroblast RBTM1 and SH-SY5Y cell (Cancer Research, vol. 58, pp 2158–2165, 1998) are cultured in RPMI1640 (GibcoBRL) containing 10% inactivated fetal bovine serum. The induction of differentiation to neural cell is achieved by the treatment with all-trans type of retinoic acid (Sigma; which are cultured at a final concentration of 5 µmol/ml for 7 days). The cells should be always cultured within plastic plates (Sumitomo Bakelite).

(2) General Method for the Preparation of Primary Culture of Rat Brain Cells

Primary culture cells from rat brain are cultured in D-MEM (Gibco BRL) containing 5% inactivated fetal bovine serum and 5% inactivated horse serum (Gibco BRL). Primary culture cells are prepared by the following method. SD rats on days 18 of gestation are deeply anesthetized with diethylether and then euthanized by blood letting from the axillary artery. After the death is confirmed, the uterus together with fetuses is resected by celiotomy. The brains are obtained from the heads of aseptically resected fetuses from the uterus and allowed to stand in a working solution (containing 50% D-MEM, 50% PBS (Gibco BRL), 5×10₄ U/L penicillin (Gibco BRL), and 50 mg/L streptomycin (Gibco BRL)). Then the part of brain stem and meninges on the cerebral hemisphere are removed under a stereoscopic microscope. The brain tissue was washed once with the working solution and then cut into strips with a surgical knife. After treated with papain (the treatment is performed by mixing them, while repeatedly inverting, in a solution containing 1.5 U/ml papain (Worthington Biochem), 0.2 mg/ml cysteine (Nacarai), 0.2 mg/ml bovine serum albumin (Sigma), 5 mg/ml glucose (Wako), and 0.1 mg/ml DNase I (Gibco BRL) at 32° C. for 30 minutes), the cells are suspended by pipetting and harvested by centrifugation (at 120 rpm for five minutes). The recovered brain cells are washed twice with D-MEM containing 5% inactivated horse serum, 5% inactivated fetal bovine serum, 5×10⁴ U/L penicillin, and 50 mg/L streptomycin. Then, the cell count was determined and the cells are plated on a 6-well plate coated with poly-L-lysine (CellTight PL, Sumitomo Bakelite) at a cell density of 1–3×10⁶ per well and cultured in a $CO_2$ incubator (at 37° C. in an atmosphere of 5% $CO_2$).

(3) Transfection

All the procedures in transfection experiments were carried out by using LIPOFECTAMINEPLUS (Gibco BRL) according to the attached instruction. 293T cells were plated on a 6-well plastic plate (Sumitomo Bakelite) at a cell density of 5×10⁵ per well and cultured in a $CO_2$ incubator (at 37° C. in an atmosphere of 10% $CO_2$ gas) for 48 hours. The culture medium was changed with 800 µl/well OptiMEM (Gibco BRL) 30 minutes before the transfection, and then the culture was continued. The amounts of DNAs used for transfection were 300 ng/well gene transfer vectors and 600 ng/well packaging vector or blank vector. After DNAs were dissolved in 100 µl OptiMEM, 6 µl PLUS reagent (Gibco BRL) was added thereto, stirred, and allowed to stand at room temperature for 15 minutes. 4 µl aliquot of LIPO-FECTAMINE, diluted with 100 µl OptiMEM, was added to the mixture of DNA and PLUS reagent (Gibco BRL), stirred, and then allowed to stand at room temperature for another 15 minutes. The solution prepared by the method described above containing the complex of DNA and LIPO-FECTAMINE was instilled to 293T cells cultured on the 6-well plate, stirred gently, and then incubated in a $CO_2$ incubator (at 37° C. in an atmosphere of 10% $CO_2$ gas) for 3 hours. After the culture was completed, 1 ml D-MEM containing 20% inactivated fetal bovine serum per well was added to the culture and then incubated in a $CO_2$ incubator (at 37° C. in an atmosphere of 10% $CO_2$ gas) for 48 hours to be used for β-galactosidase and luciferase assay.

(4) β-Galactosidase and Luciferase Assay

β-Galactosidase and luciferase assays were carried out using a Luminescent beta-gal detection kit II (Clontech) and a Luciferase Assay System (Promega), respectively, according to the attached instructions. The sample used was cell lysate, which was obtained by lysing DNA-transfected 293T cells with 800 μl/well Reporter Lysis Buffer, centrifuging at 12000 g at 4° C. for five minutes, and separating the supernatant. In β-galactosidase assay, 20 μl cell lysate and 100 μl substrate solution were mixed together and then allowed to stand still at room temperature for one hour, followed by the measurement of the intensity of luminescence for 10 seconds with a luminometer (AutoLumat LB953, berthold). In luciferase assay, 20 μl cell lysate and 100 μl substrate solution were mixed together and immediately the intensity of luminescence was measured for 10 seconds with a luminometer (AutoLumat LB953,berthold). In both of assays, each measurement was carried out with triplicate samples to determine the averaged value and standard deviation.

(5) PCR

All the procedures in PCR experiments were carried out by using PCR Supermix High Fidelity (Gibco BRL). 1 μg template DNA as a substrate and two synthetic oligonucleotides as primers, which were used at a final concentration 1 nmol/ml, were added to 90 μl reaction solution. The total volume of the mixture was adjusted to 100 μl with distilled water and then the reaction was conducted in a thermal cycler (GeneAmp PCR System 9600; Perkin Elmer). The sample was first heated at 94° C. for one minute, then subjected to 10 cycles of 94° C. for 30 seconds, 55° C. for 30 seconds, and 68° C. for 90 seconds, and further maintained at 68° C. for five minutes. DNA was purified from the reaction solution by treating with Wizard DNA Clean-up System (Promega), digested with a desired restriction enzyme, and then separated by 1% low melting point agarose gel (SeaPlaque GTG agarose; FMC Boichem; dissolved in TAE buffer) electrophoresis. A DNA fragment with a desired size was cut off from the gel and purified by Wizard PCR Preps DNA Purification System (Promega) to use for the ligation reaction.

(6) General Method for SIVagm Vector-Mediated Gene Transfer

Target 293T cells were plated on a 6-well plastic plate (Sumitomo Bakelite) at a cell density of 5×10⁵/well and then cultured in a CO₂ incubator (at 37° C. in an atmosphere of 10% CO₂ gas) for 48 hours to use for the assay. The vector-containing solution, containing Polybrene (Sigma) at a final concentration of 8 μg/ml, was layered into target cells for introducing the vector. 48 hours after the infection of the vector, the target cells were stained by using X-gal as a substrate with a Beta-Gal Staining Kit (Invitrogen) and then observed under an inverted microscope (DMIRB(SLR); Leica) to detect the expression of β-galactosidase in the target cells. The number of cells stained blue with X-gal is determined, and a vector amount that allows a single 293T cell to express β-galactosidase is calculated as 1 Transducing Unit (TU).

(7) General Method Staining of Gene Transferred-Cells with Antibody 48 hours after the infection of the vector, the target cells are washed with PBS (Nikken Biological and Medical Institute), fixed with PBS containing 4% paraformaldehyde (Wako) at room temperature for 30 minutes, washed three times with PBS for five minutes, and then subjected to the blocking with PBS containing 2% normal goat serum (Gibco BRL) at room temperature for one hour. As a primary antibody for differentiated neuron derived from the rat brain, a solution prepared by diluting an anti-MAP-2 monoclonal antibody (mouse IgG, BOEHRINGER MANHEIM) to 2 μg/ml with PBS containing 2% normal goat serum is used. As a primary antibody for cells into which β-galactosidase is introduced, a solution prepared by diluting an anti-E. coli β-galactosidase polyclonal antibody (rabbit; 5 prime ->3 prime Inc.) to 8.2 μg/ml with PBS containing 2% normal goat serum is used. The reaction is carried out at 37° C. for 30 minutes. After reaction of the primary antibody, the cells are washed three times with PBS for five minutes and, then, are reacted with a secondary antibody. 10 μg/ml anti-mouse IgG polyclonal antibody (goat; EY LABORATORIES, INC.) labeled with Texas Red, or 4 μg/ml anti-mouse IgG polyclonal antibody labeled with Alexa568 (goat; Molecular Probes, Inc.), both of which is diluted with PBS containing 2% normal goat serum, is used as the secondary antibody for rat brain cells with introduced EGFP;. On the other hand, anti-mouse IgG polyclonal antibody (goat; Molecular Probes, Inc.) labeled with Alexa488 and anti-rabbit IgG polyclonal antibody (goat; Molecular Probes, Inc.) labeled with Alexa568, each of which is diluted with PBS containing 2% normal goat serum to 4 μg/ml, are used as for rat brain cells with introduced β-galactosidase. 4 μg/ml goat anti-rabbit IgG polyclonal antibody labeled with Alexa568, diluted with PBS containing 2% normal goat serum, is used for cells with introduced β-galactosidase other than rat brain cells. All the reactions with secondary antibody are conducted at 37° C. for 30 minutes. After the reaction with secondary antibody, the target cells are washed three times with PBS for five minutes, PBS is layered thereon, and then the fluorescence is observed under an inverted microscope (DMIRB (SLR); Leica) to detect the expression of protein of interest.

INDUSTRIAL APPLICABILITY

The present invention provides vectors capable of expressing two foreign genes by using RRE sequence. The ratio between the expression levels of two foreign genes can be adjusted in the present vector by modifying the RRE sequence. In addition, the dependency on virus-derived protein can be overcome by modifying the virus-derived regulatory sequence for expression to those derived from others. The risk of reversion to the wild type via gene recombination is reduced and thus the safety is enhanced by using the minimal region containing the packaging signal for the vector. The present vector is suitable for use in gene therapy, etc.

What is claimed is:

1. A vector DNA for expressing two foreign genes, said vector DNA comprising the following components in order from the 5' side to the 3' side:
   (a) an expression regulatory sequence;
   (b) a splicing donor sequence;
   (c) a first foreign gene insertion site;
   (d) an RRE core sequence;
   (e) a splicing acceptor sequence; and
   (f) a second foreign gene insertion site,
and said vector DNA further comprising a packaging signal, in which the translation initiation codon of a gag protein is mutated.

2. The vector DNA of claim 1, wherein said RRE core sequence comprises a retrovirus, a lentivirus, or an immunodeficiency virus RRE core sequence.

3. The vector DNA of claim 1, wherein said expression regulatory sequence comprises an LTR.

4. The vector DNA of claim 1, wherein said expression regulatory sequence is a sequence comprising an expression regulatory sequence other than an LTR.

5. The vector DNA of claim 4, wherein said expression regulatory sequence other than an LTR is selected from the group consisting of the CMVL promoter, the CMV promoter, and the EF1 α promoter.

6. The vector DNA of claim 1, wherein each of said splicing donor sequence and said splicing acceptor sequence comprise a retrovirus, a lentivirus, or an immunodeficiency virus sequence.

7. The vector DNA of claim 1, wherein said packaging signal is in a region thereon that can be transcribed.

8. The vector DNA of claim 7, wherein said packaging signal comprises a retrovirus, a lentivirus, or an immunodeficiency virus packaging signal.

9. The vector DNA of claim 1, wherein a first foreign gene and a second foreign gene are inserted into said vector DNA.

10. A retrovirus vector comprising, within a virus particle thereof, a transcription product from the vector DNA according to claim 1, wherein a first foreign gene and a second foreign gene have been inserted into said vector DNA.

11. A lentivirus vector comprising, within a virus particle thereof, a transcription product from the vector DNA according to claim 1, wherein a first foreign gene and a second foreign gene have been inserted into said vector DNA.

12. An immunodeficiency virus vector comprising, within a virus particle thereof, a transcription product from the vector DNA according to claim 1, wherein a first foreign gene and a second foreign gene have been inserted into said vector DNA.

13. A method for preparing a virus vector, said method comprising the steps of introducing into a packaging cell the vector DNA according to claim 1, wherein a first foreign gene and a second foreign gene are inserted into said vector DNA, and collecting produced virus particles from a culture supernatant of said cell.

14. A vector DNA for expressing two foreign genes, said vector DNA comprising the following components in order from the 5' side to the 3' side:
(a) an expression regulatory sequence;
(b) a splicing donor sequence;
(c) an RRE core sequence;
(d) a first foreign gene insertion site;
(e) a splicing acceptor sequence; and
(f) a second foreign gene insertion site.

15. The vector DNA of claim 14, wherein said RRE core sequence comprises a retrovirus, a lentivirus, or an immunodeficiency virus RRE core sequence.

16. The vector DNA of claim 14, wherein said expression regulatory sequence comprises an LTR.

17. The vector DNA of claim 14, wherein said expression regulatory sequence is a sequence comprising an expression regulatory sequence other than an LTR.

18. The vector DNA of claim 17, wherein said expression regulatory sequence other than an LTR is selected from the group consisting of the CMVL promoter, the CMV promoter, and the EF1α promoter.

19. The vector DNA of claim 14, wherein each of said splicing donor sequence and said splicing acceptor sequence comprise a retrovirus, a lentivirus, or an immunodeficiency virus sequence.

20. The vector DNA of claim 14, wherein said vector DNA further comprises a packaging signal in a region thereon that can be transcribed.

21. The vector DNA of claim 20, wherein said packaging signal comprises a retrovirus, a lentivirus, or an immunodeficiency virus packaging signal.

22. The vector DNA of claim 21, wherein said vector DNA is constructed so as not to express a complete gag protein.

23. The vector DNA of claim 22, wherein the translation initiation codon of said gag protein is mutated.

24. The vector DNA of claim 14, wherein a first foreign gene and a second foreign gene are inserted into said vector DNA.

25. A retrovirus vector comprising, within a virus particle thereof, a transcription product from the vector DNA according to any one of claims 20 to 23, wherein a first foreign gene and a second foreign gene have been inserted into said vector DNA.

26. A lentivirus vector comprising, within a virus particle thereof, a transcription product from the vector DNA according to any one of claims 20 to 23, wherein a first foreign gene and a second foreign gene have been inserted into said vector DNA.

27. An immunodeficiency virus vector comprising, within a virus particle thereof, a transcription product from the vector DNA according to any one of claims 20 to 23, wherein a first foreign gene and a second foreign gene have been inserted into said vector DNA.

28. A method for preparing a virus vector, said method comprising the steps of introducing into a packaging cell the vector DNA according to any one of claims 18 to 21, wherein a first foreign gene and a second foreign gene are inserted into said vector DNA, and collecting produced virus particles from a culture supernatant of said cell.

* * * * *

UNITED STATES PATENT AND TRADEMARK OFFICE
CERTIFICATE OF CORRECTION

PATENT NO. : 6,979,568 B1
APPLICATION NO. : 09/980420
DATED : December 27, 2005
INVENTOR(S) : Toshihiro Nakajima et al.

It is certified that error appears in the above-identified patent and that said Letters Patent is hereby corrected as shown below:

On the cover sheet, in "References Cited", under "U.S. PATENT DOCUMENTS", insert the following:
-- 5,739,118 A  4/1998  Carrano et al.
   6,197,755 B1 3/2001  Carrano et al. -- .

Column 9, line 43, replace "SIVagmTYo1" with --SIVagmTYO1--.

Column 12,
Line 36, replace "7- (1R" with --7-1R--; and
Line 65, replace "8- (1R" with --8-1R--.

Column 13, Line 19, replace "pSA212as" with --pSA212 as--.

Column 25, Line 4, replace "EF1 α" with --EF1α--.

Signed and Sealed this

Eighth Day of August, 2006

JON W. DUDAS
*Director of the United States Patent and Trademark Office*